United States Patent [19]

Andrews et al.

[11] Patent Number: 5,275,996
[45] Date of Patent: Jan. 4, 1994

[54] PHOSPHOROUS/VANADIUM OXIDE CATALYST AND PROCESS OF PREPARATION THEREOF

[75] Inventors: William J. Andrews, Hazelwood; Jerry R. Ebner, St. Peters; Timothy R. Felthouse, St. Louis, all of Mo.

[73] Assignee: Monsanto Company, St. Louis, Mo.

[21] Appl. No.: 887,254

[22] Filed: May 22, 1992

[51] Int. Cl.$^5$ .......................................... B01J 27/198
[52] U.S. Cl. ................................................ 502/209
[58] Field of Search ..................................... 502/209

[56] References Cited

U.S. PATENT DOCUMENTS

| | | | |
|---|---|---|---|
| 3,864,280 | 2/1975 | Schneider | 252/435 |
| 4,092,269 | 5/1978 | Mount et al. | 252/435 |
| 4,187,235 | 2/1980 | Katsumoto et al. | 260/346.75 |
| 4,251,390 | 2/1981 | Barone | 252/435 |
| 4,315,864 | 2/1982 | Bremer et al. | 260/346.75 |
| 4,328,162 | 5/1982 | Hyatt et al. | 260/397.45 |
| 4,333,853 | 6/1982 | Milberger et al. | 252/435 |
| 4,386,215 | 5/1983 | Mount et al. | 502/209 X |
| 4,567,158 | 1/1986 | Wrobleski et al. | 502/209 |
| 4,632,915 | 12/1986 | Keppel et al. | 502/209 |
| 4,632,916 | 12/1986 | Bither, Jr. | 502/209 |
| 4,699,985 | 10/1987 | Bither, Jr. | 549/260 |
| 4,784,981 | 11/1988 | Alpers et al. | 502/209 |

OTHER PUBLICATIONS

Zazhigalow et al, *Journal of Applied Chemistry USSR*, 61 97-101 (1988).
Brunauer et al, *Journal of the American Chemical Society*, 60, 309-319 (1938).

Primary Examiner—W. J. Shine
Attorney, Agent, or Firm—W. W. Brooks

[57] ABSTRACT

An activated porous phosphorus/vanadium oxide catalyst adapted for the catalytic oxidation of a hydrocarbon to produce a carboxylic acid anhydride. The catalyst comprises shaped bodies having a B.E.T. surface area of at least about 15 m$^2$/g, an average vanadium oxidation state of between about 4.0 and about 4.5, a total pore volume of at least about 0.15 cc/g, a normalized apparent shaped body density of between about 1.25 and about 2.0 g/cc, and a crush strength of at least about 4 pounds. At least about 5% of the pore volume of the catalyst is constituted of pores having a diameter of at least about 0.8 microns, and at least about 4% of the pore volume is constituted of pores having a diameter of at least about 10 microns. The catalyst is prepared by mixing a particulate phosphorus/vanadium oxide precursor with a pore modification agent to produce a modified catalyst precursor composition, forming the modified precursor composition into a predetermined shape, and removing the pore modification agent substantially at a temperature below 300° C.

40 Claims, 14 Drawing Sheets

PHOSPHOROUS/VANADIUM OXIDE CATALYST AND PROCESS OF PREPARATION THEREOF

BACKGROUND OF THE INVENTION

This invention relates to phosphorus/vanadium oxide catalysts useful in a process for the oxidation of hydrocarbons to dicarboxylic acid anhydrides, and more particularly to a high surface area catalyst of improved microstructure which provides high yields in such a process. The invention is also directed to a method for the preparation of the catalyst.

Numerous catalysts containing vanadium, phosphorus and oxygen (sometimes referred to as mixed oxides of vanadium and phosphorus), substantially in the form of vanadyl pyrophosphate, optionally containing a promoter component, are disclosed in the prior art as being useful for the conversion of various hydrocarbon feed stocks to maleic anhydride. In general, such catalysts wherein the valence of the vanadium is less than $+5$, usually between about $+3.8$ and about $+4.8$, are considered particularly well suited for the production of maleic anhydride from hydrocarbons having at least four carbon atoms in a straight chain (or cyclic structure). Typically, such catalysts also contain promoter elements or components which are considered to be present in the catalyst as oxides. Common organic feed stocks include non-aromatic hydrocarbons such as n-butane, 1- and 2-butenes, 1,3-butadiene, or mixtures thereof.

Generally, such catalysts are prepared by contacting vanadium-containing compounds, phosphorus-containing compounds, and promoter component-containing compounds (when a promoter element is desired) under conditions sufficient to reduce pentavalent vanadium to the tetravalent state and form the desired catalyst precursor comprising vanadyl hydrogen phosphate, optionally containing a promoter component. The catalyst precursor is thereafter recovered, typically in particulate form, and subjected to a variety of further conventional processing techniques to produce the active catalyst. An essential step in such further processing is calcination. Prior to calcination, the catalyst is typically formed into a shaped body such as tablet or pellet by compression in a die. A lubricant is ordinarily incorporated in the precursor composition to facilitate the tableting or pelletizing process.

In its final form, the catalyst comprises a mass of porous tablets or pellets which are charged in bulk to provide the catalyst bed of a fixed bed reactor. Typically, the catalyst is charged to a tubular reactor comprising the tubes of a shell and tube heat exchanger. Hydrocarbon and oxygen are fed to the tubes, and a heat transfer fluid, such as molten salt, is circulated through the shell to remove the exothermic heat of the oxidation reaction. The porous nature of the catalyst contributes substantially to the active surface area at which the catalytic reaction takes place. However, for the internal surfaces of the catalyst body (tablets or pellets) to be utilized effectively, the feed gases, hydrocarbon and oxygen, must diffuse through the pores to reach the internal surfaces, and the reaction products must diffuse away from those surfaces and out of the catalyst body.

It is known in the art that resistance to internal diffusion in the catalyst bodies can become a rate limiting factor in the reaction. The diffusion paths can be shortened (and catalyst body external surface increased) by using relatively small catalyst granules. However, in this case better mass transfer is purchased at a sacrifice in pressure drop through the fixed bed. Thus, a need has existed in the art for a phosphorus/vanadium oxide catalyst having a microstructure such that internal diffusion resistance is minimized and productivity is enhanced at constant granule size and pressure drop.

Zazhigalov, et al, "Effect of the Pore Structure and Granule Shape of V-P-O Catalyst on the Selectivity of Oxidation of n-Butane," *Zhurnal Prikladnoi Kimii*, Vol. 61, No. 1, pp. 101-105 (January, 1988) reports that the activity of V-P-O catalysts in the oxidation of n-butane increases with an increase in the total pore volume and macropore volume. Zazhigalov et al further describe the use of polyethylene oxide as a pore forming additive in the preparation of V-P-O catalyst to produce granules having a greater proportion of macropores. The pore builder is apparently incorporated in the catalyst precursor formulation, and later removed from the catalyst by burning it out in the calcination step. This process produces a catalyst having a proportion of macropores significantly greater than was realized without the pore builder. However, despite the previously recognized advantage of macropores, test reactor experiments show that the addition of polyethylene oxide resulted in a decrease in the efficiency of the catalyst. Zazhigalov et al. explains these results by assuming that, after burn-up of the polymer, a dense film of coke remains on the surface of the catalyst and deactivates the active centers of the catalyst. They confirmed that hypothesis by the detection of $CO_2$ that was liberated when the catalyst was heated (873° K.) in an air current.

Mount et al. U.S. Pat. No. 4,092,269 is directed to a phosphorus/vanadium oxygen catalyst prepared by reaction of phosphoric acid, phosphorus acid and vanadium pentoxide in an aqueous medium to produce a catalyst precursor, which is converted to an active catalyst by calcination. The catalyst produced contains predominantly pentavalent vanadium, generally having an average vanadium oxidation state of about $+4.6$ or more. The B.E.T. surface area of the Mount catalyst is about 8 $m^2/g$ or less, and the pore volume of the catalyst from pores having diameters between about 0.8 microns and about 10 microns is greater than 0.02 cc/g. Preferably, the volume constituted of pores having diameters between 1 and 5 microns is at least about 0.03 cc/g. However, Mount states that catalysts having a pore volume from pores having diameters larger than about 10 microns have virtually no effect on the yield of maleic anhydride using such catalysts. Catalysts having Mount's desired fraction of 0.8 to 10 micron macropores are prepared by adding a pore modification agent to the precursor at any stage prior to calcination. Calcination of the precursor containing the pore modification agent is conducted at a temperature between about 300° and 600° C. A lengthy list of pore modification agents is disclosed, including adipic acid, citric acid, oxalic acid, stearic acid, polyethylene glycol, polyvinyl alcohol, polyacrylic acid, cellulosic materials, monosaccharides, polysaccharides, hydrogenated vegetable oils, waxes, and gelatin. Cellulosic materials and hydrogenated vegetable oils are preferred, and methylcellulose especially preferred. The Mount et al. reference states that the yield of maleic anhydride using a phosphorus/-vanadium oxide catalyst is significantly improved by controlling the pore size distribution of the finished catalyst in the ranges discussed above. In the working examples of Mount et al., the pore modification agent is removed by calcining at 380° to 500° C.

Bither U.S. Pat. No. 4,699,985 describes the preparation of a maleic anhydride catalyst in which a precursor catalyst is blended with 3 to 5% by weight of an organic pore modifying agent, and with fumed silica in an amount of 0.05 to 0.20% by weight. Upon firing of the blend, the organic pore modifying agent and the fumed silica generate a catalyst microstructure which is said to lead to enhanced production of maleic anhydride. Pore builders disclosed as suitable include organic acids, polymeric materials, cellulosic materials, monosaccharides and polysaccharides, hydrogenated vegetable oils and waxes. A preferred pore builder is Sterotex hydrogenated cottonseed oil. The pore modifying agent also serves as a lubricant in preparing shaped catalyst particles. According to the disclosure, the precursor blend is fired in a controlled manner to generate and activate the catalyst species. Precursor catalyst pellets are heated in a low flow of air at 375° to 400° C. for 1 to 6 hours, and thereafter in a more rapid flow of 1 to 1.5% n-butane in air at 450° to 490° C. for an additional 16-24 hours. In a preferred method, the shaped catalyst precursor blend is initially fired in a continuous zoned belt furnace in an air atmosphere. The temperature varies from ambient at the furnace ends to 390° to 395° C. at the center of the heated zone. Air diffuses through baffles at the ends of the furnace to replace combustion products diffusing out through vertical vents located in the heated zone of the furnace.

Methods have been developed in the art for the preparation of high surface area catalysts by reaction of vanadium pentoxide and a phosphorus compound in an organic medium. The surface area of these catalysts is generally in the range of 15 m²/g or greater as determined by the method of Brunauer, Emmett and Teller, *J. Am. Chem. Soc.*, 60, 309 (1938). Surface area as determined by this method is generally referred to in the art as "B.E.T." surface area. Methods for producing high surface area catalysts are described, for example, in U.S. Pat. Nos. 4,632,916; 4,632,915; 4,567,158; 4,333,853; 4,315,864; 4,328,162; 4,251,390; 4,187,235; and 3,864,280.

Copending and coassigned application Ser. No. 07/722,070, filed Jun. 27, 1991, now U.S. Pat. No. 5,137,860 describes a process for the transformation of a catalyst precursor represented by the formula:

into an active catalyst represented by the formula:

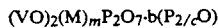

where M is at least one promoter element selected from the group consisting of elements from Groups IA, IB, IIA, IIB, IIIA, IIIB, IVA, IVB, VA, VB, VIA, VIB, and VIIIA of the periodic table, and mixtures thereof, m is a number from zero (0) to about 0.2, a is a number of at least about 0.5, b is a number taken to provide a P/V atom ratio of from about 1.0 to about 1.3, c is a number representing the oxidation number of phosphorus and has a value of 5, and n is a number taken to represent the weight % of intercalated organic components in the precursor. In transforming the precursor to the active catalyst, the precursor is heated in an atmosphere of air, steam, inert gas, and mixtures thereof to a temperature not greater than about 300° C. The catalyst precursor is maintained at such temperature under an atmosphere containing molecular oxygen, steam, and optionally an inert gas, the atmosphere being represented by the formula $(O)_x(H_2O)_y(IG)_z$ where IG is an inert gas and x, y, and z represent mol percentages of the $O_2$, $H_2O$, and IG components, respectively, in the molecular oxygen/steam-containing atmosphere, x having a value greater than zero (0) mol percent, y having a value greater than zero (0) mol % but less than 100 mol %, and z having a value representing the balance of the molecular oxygen/steam-containing atmosphere. The temperature is increased at a programmed rate of from about 2° C./min. to about 12° C./min. to a value effective to eliminate the water of hydration from the catalyst precursor. The temperature is then adjusted to a value greater than 350° C., but less than 550° C. and the adjusted temperature is maintained in the molecular oxygen/steam-containing atmosphere for a time effective to provide a vanadium oxidation state of from about +4.0 to about +4.5. The adjusted temperature is maintained thereafter in a non-oxidizing, steam-containing atmosphere for a time effective to complete the catalyst precursor-to-active catalyst transformation to yield the active catalyst.

SUMMARY OF THE INVENTION

Among the several objects of the present invention, therefore, may be noted the provision of an improved phosphorus/vanadium oxide catalyst effective in the catalytic oxidation of hydrocarbons, more particularly the catalytic oxidation of $C_4$ hydrocarbons to maleic anhydride; the provision of such a catalyst which is permeable to relatively rapid internal diffusion of reactant and product gases; the provision of such a catalyst which may be used to produce maleic anhydride at high productivity but low pressure drop; and the provision of a process for the preparation of such a catalyst.

Briefly, therefore, the present invention is directed to an activated porous phosphorus/vanadium oxide catalyst adapted for the catalytic oxidation of a hydrocarbon to produce a carboxylic acid anhydride. The catalyst comprises shaped bodies having a B.E.T. surface area of at least about 15 m²/g, an average vanadium oxidation state of between about 4.0 and about 4.5, a total pore volume of at least about 0.15 cc/g, a normalized apparent shaped body density of between about 1.0 and about 2.0 g/cc, and a crush strength of at least about 4 pounds. At least about 5% of the pore volume of the catalyst is constituted by pores having a diameter of at least about 0.8 microns and at least about 4% of the pore volume is constituted of pores having a diameter of at least about 10 microns.

The invention is further directed to a process for the preparation of a phosphorus/vanadium oxide catalyst. In the process, a modified catalyst precursor composition is prepared comprising a mixture of a particulate phosphorus/vanadium oxide catalyst precursor composition and a pore modification agent. The pore modification agent is subject to vaporization, decomposition or oxidation at a temperature below 300° C. without leaving a substantial residue. The modified precursor composition is formed into a predetermined shape under compression, thereby producing a shaped porous catalyst precursor body comprising the precursor composition and containing the pore modification agent. The pore modification agent is removed from the shaped body substantially at a temperature below 300° C., thereby producing a precursor catalyst body having a pore volume of at least about 0.15 cc/g. At least about 5% of the pore volume of the body is constituted of pores having a diameter of at least about 0.8 microns and at least about 4% of the pore volume is constituted of pores having a diameter of at least about 10 microns.

The invention is further directed to a process for the preparation of a phosphorus/vanadium oxide catalyst in which a modified catalyst precursor composition is prepared comprising a mixture of a particulate phosphorus/vanadium oxide catalyst precursor composition and a particulate pore modification agent. The mean particle diameter of the pore modification agent is not greater than about two orders of magnitude different from the mean particle diameter of the precursor composition. The modified precursor composition is formed into a predetermined shape under compression, thereby producing a shaped porous catalyst precursor body comprising the precursor composition and containing the pore modification agent. The agent is removed from the body substantially at a temperature below 300° C., thereby producing a precursor catalyst body having a pore volume of at least about 0.15 cc/g.

Other objects and features will be in part apparent and in part pointed out hereinafter.

DESCRIPTION OF THE PREFERRED EMBODIMENTS

Figure 1:
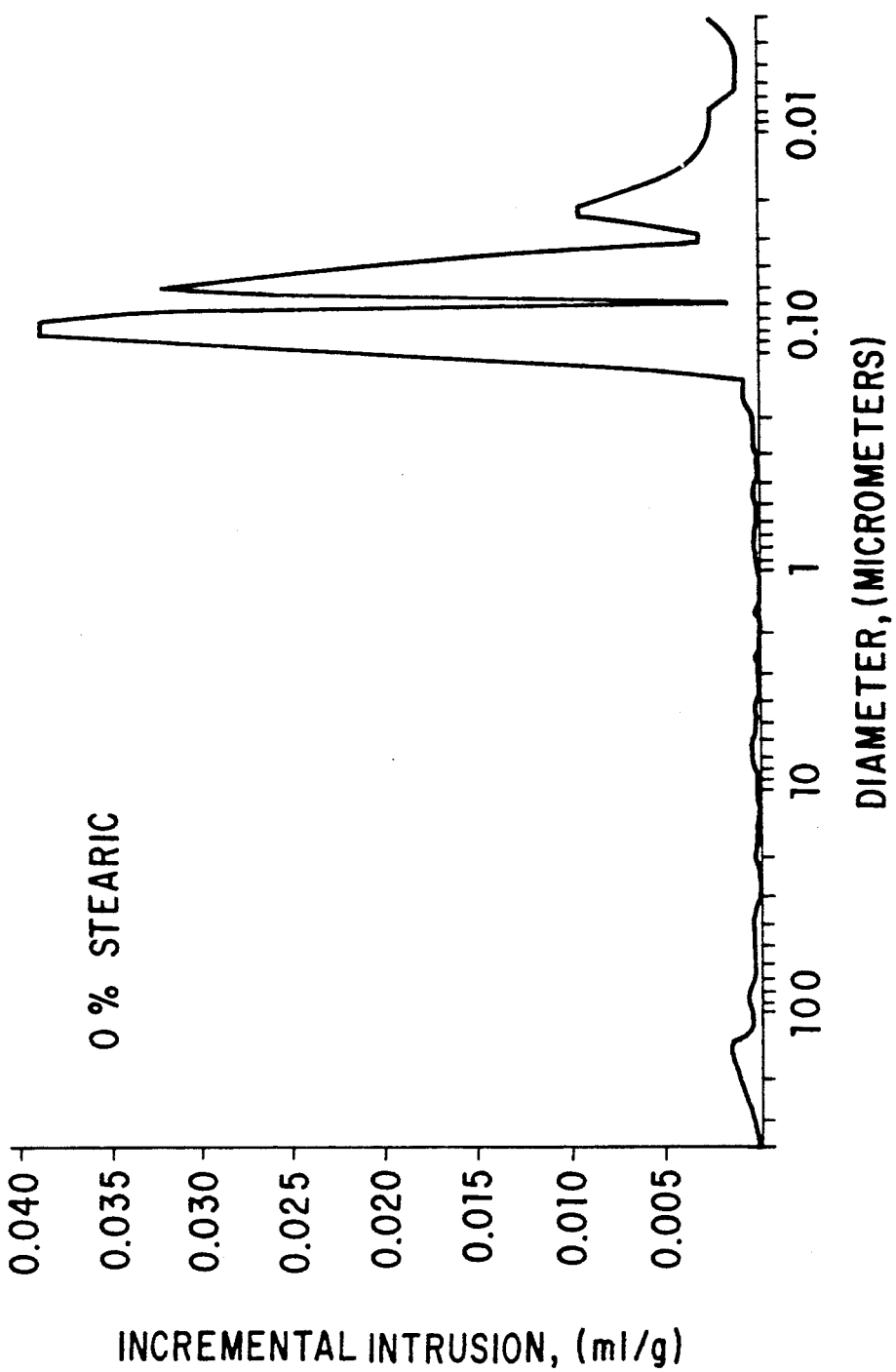
FIG. 1 is a plot of the distribution of pore volume as a function of pore diameter in a vanadium/phosphorus oxide catalyst prepared by ANST activation of a tabletted catalyst precursor composition containing no pore modification agents.
Figure 2:
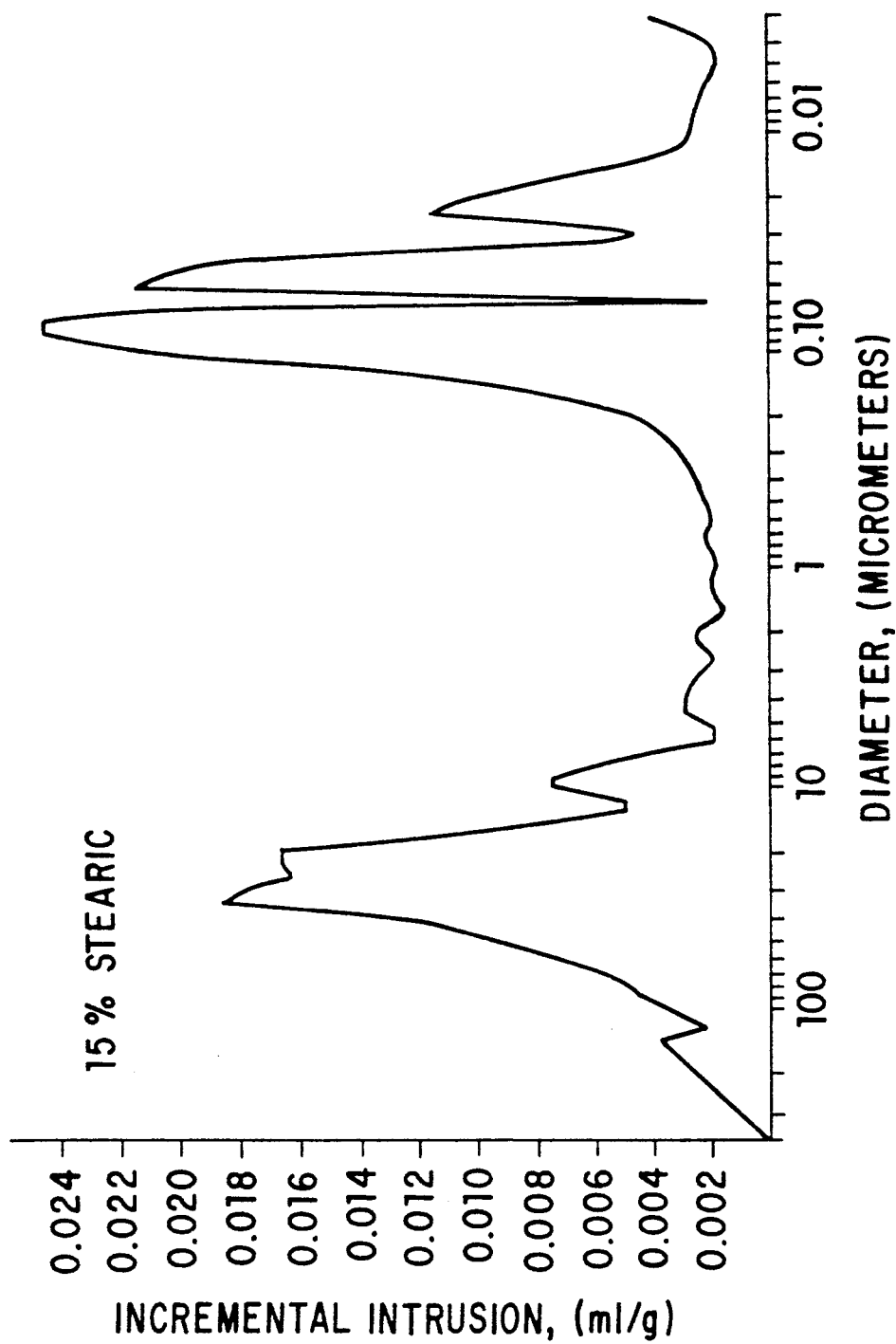
FIG. 2 is a plot showing a pore distribution of a vanadium/phosphorus oxide catalyst prepared by ANST thermal treatment of a tabletted catalyst precursor composition containing 15% by weight of a mixture of stearic acid, palmitic acid and myristic acid in the pores thereof.

In accordance with the invention, it has been discovered that enhanced productivity in the conversion of n-butane or other hydrocarbons to maleic anhydride is achieved by using a high surface area porous phosphorus/vanadium oxide catalyst which has been prepared using a pore builder to produce a high proportion of large pores therein. Catalysts of the invention contain primarily tetravalent vanadium, having a an average vanadium oxidation state of 4.0 to 4.5, preferably 4.06 to 4.30, and comprise tablets, pellets or other shaped bodies having a B.E.T. surface area of at least about 15 m$^2$/g. Such high surface area results from a high concentration of pores having an average pore diameter of less than about 0.05 microns. By the further presence of a high concentration of macropores having a pore diameter of in the range of about 0.8 to about 10 microns and above, means are provided for rapid internal diffusion of product and reactant gases within the catalyst body. The large pores constitute flow arteries for distribution of these gases, thereby providing access of reaction gases to the active surfaces of the catalyst and egress of product gases from the finer pores of the catalyst body. This rapid exchange of gases allows maximum effective use of more of the internal surface of the tablet or pellet in the catalytic oxidation of C$_4$ hydrocarbons to maleic anhydride.

Total pore volume of the catalyst of the invention is at least about 0.15 cc/g, preferably at least about 0.18 cc/g. Of the total pore volume, at least about 5%, preferably at least about 8%, is constituted of pores having a diameter greater than 0.8 micron. Generally, the proportion of pore volume constituted of 0.8+ micron pores is between about 8% and about 50%, preferably between about 10% and about 30%. Advantageously, the catalyst of the invention further contains a substantial volume of pores having a diameter greater than 10 microns. Of the total pore volume, at least about 4%, preferably at least about 6%, is constituted of pores having a diameter greater than 10 microns. Most preferably, the volume constituted by pores of greater than about 10 microns is between about 6% and about 40% of the total pore volume.

Because of the rapid internal diffusion afforded by the pore distribution within the catalyst, reactant gases can diffuse to the centers of even relatively large bodies for effective utilization of the entire internal surface thereof. This allows the catalyst to be produced in large tablets or pellets, resulting in low pressure drop through a catalyst bed without sacrificing productivity to the inaccessibility of internal surfaces.

A substantial volume of macropores is obtained by using a pore modification agent in the preparation of the catalyst tablets or pellets. By employing relatively mild conditions in generating the macropores, the desired pore size distribution is realized without adversely affecting the activity at the active internal surfaces of the catalyst. Such advantageous results are realized by both selection of the pore modification agent and control of the conditions under which the pore modification agent is removed from the catalyst.

Catalysts prepared by the process of the invention also exhibit crush strengths satisfactory for use in commercial reactors, for example, for the production of maleic anhydride by catalytic oxidation of n-butane. Gravity and other compaction forces tend to crush porous catalyst bodies to a powder form, which results in high pressure drop through the catalyst bed. Inadequate crush strength is generally associated with low apparent density of the catalyst bodies. Despite their high total pore volume and large proportion of macropores, the activated catalyst bodies of the invention have been found to exhibit a substantial normalized apparent shaped body density, in the range of between about 1.0 and about 2.0 g/cc, and a crush strength of at least about 4 pounds, more typically at least about 8 pounds. Normalized apparent shaped body density is the same as measured apparent density where the solid phase of the catalyst is entirely constituted of phosphorus/vanadium oxide catalyst. Where the solid phase contains a foreign material such as, for example, a particulate iron aggregate, the normalized apparent density is determined by adjusting the measured apparent density for the weight fraction of VPO in the catalyst body. Thus, if:

$a_n$ = the normalized apparent body density
$a_m$ = the measured apparent body density
$x$ = the weight fraction VPO in the catalyst body then:

$$a_n = a_m x$$

Where no aggregate is present, the normalized (and measured) apparent body density is between about 1.25 and about 2.0 g/cc.

In the process of the invention, a modified catalyst precursor composition is prepared comprising a mixture of a particulate phosphorus/vanadium oxide catalyst precursor composition and a pore modification agent which is subject to removal from the catalyst after tableting or pelletizing. The pore modification agent should be substantially chemically inert with respect to the precursor composition and subject to removal under mild conditions from the catalyst precursor body. More particularly, the pore modification agent should be removable without exposing the precursor composition to an exotherm of such severity as to cause premature or uncontrollably rapid dehydration. To facilitate its removal under relatively mild conditions, the pore modification agent should be subject to vaporization, decomposition or oxidation at temperatures below 300° C. and without leaving a substantial carbon, ash, or other residue. In particular, it is essential that the mechanism of removal of the pore modification agent be substantially quantitative without generating an exotherm, whether due to decomposition or reaction with the atmosphere in which removal takes place, which would heat the catalyst Precursor composition above 300° C. for any significant period of time.

A preferred type of pore modification agent is thermally stable and has a substantial vapor pressure at a temperature below 300° C. It is particularly preferred that the pore modification agent have a vapor pressure of at least about 1 mm Hg at a temperature between about 150° C. and about 250° C., more preferably between about 150° C. and about 200° C.

Although pore builders which sublime may be used, it is preferred that the pore builder become molten before a substantial fraction of it vaporizes. Melting of the pore builder is believed to result in flow of the melt through the catalyst body and thereby contribute to the development of an array or network of large pores, which may then serve as arteries for internal diffusion of product and reaction gases during use of the catalyst in a gas phase oxidation reaction. Accordingly, the melting point of the agent is preferably below 150° C. but above room temperature. Advantageously, the melting point is below the temperature at which the pore modification agent becomes molten under compression in tableting or pelletizing. It is particularly preferred that the melting point be substantially lower than the temperature at which the agent is removed from the precursor body, preferably at least about 30° C. lower. Favored pore modification agents may have a melting point between about 35° C. and about 100° C., more preferably about 50° C. to about 80° C.

Preferably, the pore modification agent is a fatty acid corresponding to the formula $CH_3(CH_2)_xCOOH$ where $x > 8$ such as stearic acid ($x = 16$), palmitic acid ($x = 14$), lauric acid ($x = 10$), myristic acid ($x = 12$), esters of such acids and amides or other functionalized forms of such acids, for example, stearamide ($CH_3(CH_2)_{16}CONH_2$). Suitable esters may include methyl esters as well as glycerides such as stearin (glycerol tristearate). Mixtures of fatty acids, which typically have melting points lower than any component of the mixture, may be especially effective. However, while fatty acids and fatty acid derivatives are generally preferred, other compositions which meet the functional requirements discussed above are also suitable for use as pore modification agents (pore builders).

Other preferred pore modification agents include polynuclear organic compounds such as naphthalene. Naphthalene melts at about 80° C. and has an appreciable vapor pressure at temperatures below 175° C. Moreover, because it lacks both functional groups and polarity, it has little or no tendency to adsorb, by either physisorption or chemisorption, to the catalyst precursor composition in the catalyst precursor body. Accordingly, quantitative removal of naphthalene is readily achieved under quite mild removal conditions.

A modified catalyst precursor composition is prepared by mixing the pore builder in particulate form with a particulate precursor composition which contains oxides of vanadium and phosphorus. Preferably, the modified precursor composition contains between about 4% and about 16%, preferably between about 8% and about 12%, by weight of pore builder. This composition is then formed under compression into a tablet or other predetermined shape. Mixing is better and tablet integrity enhanced if the mean particle diameter of the precursor approximates the mean particle diameter of the precursor composition, at least within about two orders of magnitude. Typically vanadium/phosphorus oxide precursor particles have a mean diameter in the range of between about 50 to 200 microns, most often in the range of between about 80 and 110 microns. It is generally preferred that the mean particle diameter of the pore builder be between about 50 and about 2000 microns, more preferably between about 100 and about 550 microns.

Although the particulate mixture of vanadium/phosphorus oxide precursor and pore builder can be formed directly into a precursor body which is heat treated for activation, a preferred method involves a preliminary slugging and granulation step. Thus, the modified precursor mixture is compressed to produce a slug of material, for example, in the form of a cylinder, the slug is then granulated, and the granulated composition is compressed in a die to form the tablet, pellet or other shaped precursor catalyst body. The tablet or other shaped body formed by compression comprises a structure of mixed particulate phosphorus/vanadium oxide structure and particulate pore builder.

The tablets or other shaped bodies are then heated under conditions effective for removal of the pore builder from the bodies without causing an exotherm sufficient to result in excessive premature dehydration of the vanadium/phosphorus oxide precursor composition. A variety of conditions can be utilized in removal of the pore builder, depending in significant part on its nature. Generally, it is preferred that the conditions be controlled so that the precursor bodies are not heated to a temperature higher than about 300° C., more preferably not higher than about 250° C. However, brief excursions to temperatures of 350° C. or even somewhat higher can be tolerated so long as excessive dehydration is not suffered. In most systems, dehydration is not excessive if the temperature does not rise to more than about 325° C. for more than about 5 minutes.

In those preferred embodiments in which the pore builder has a melting point significantly lower than the temperature at which it is removed, the precursor bodies are preferably heated to a temperature above the melting point but below the lowest temperature at which the pore builder is subject to substantial thermal degradation or oxidation by the catalyst precursor or components of the atmosphere to which the shaped body is exposed during heating. Preferably, the shaped body is heated to a temperature at which the vapor pressure of the pore builder is above 1 mm Hg, but well below 300° C. Most of the pore builders of interest may be removed at atmospheric pressure by heating to a temperature in the range of between about 150° C. and about 250° C. Where the pore builder has a vapor pressure of <1 mm Hg in the range of between about 150° C. to about 200° C., the shaped body is preferably heated to a temperature in the range of between about 200° C. and about 250° C. Degradation of the pore builder is minimized if the shaped body is initially contacted with a flowing gas that does not react with the pore builder at the highest temperature to which it is exposed during heating. Preferably, the stripping or purge gas is an inert gas that is substantially free of molecular oxygen, for example, nitrogen or superheated steam. The gas preferably flows over the catalyst body at a velocity of at least about 1 cm/sec., more preferably between about 10 and about 100 cm/sec. Satisfactory removal of pore builder can be realized over a wide range of pressure, including atmospheric and above. However, removal of the pore builder is facilitated if the pressure is substantially below atmospheric, for example, 25-500 mm/Hg.

Under such preferred conditions, the pore builder initially melts and flows toward the external surface of the shaped body. At the surface, and typically in the passages leading toward the surfaces, the pore builder vaporizes into the purge gas. Where the temperature of the catalyst body is high enough that the vapor pressure exceeds the total pressure, the pore builder tends to boil out of the pores of the shaped body. While this may facilitate rapid removal, vigorous boiling is preferably avoided. Most efficient results may be realized where the vapor pressure is a significant fraction of the total pressure, so that the purge gas serves as a carrier gas for efficiently stripping the pore builder from the shaped body.

In order to consistently produce a catalyst of maximum activity, it has been found important to incorporate water vapor in the stripping gas. The effect of water vapor is not entirely understood, but is believed to inhibit premature or excessive stripping of water of hydration from the precursor body crystal lattice. Preferably, the water vapor content of the stripping gas is at least about 5% by volume, more preferably between about 20% and about 80% by volume, most preferably between about 30% and about 70% by volume. The presence of water vapor in the stripping gas is particularly important in the higher temperature portions of the stripping operation, and especially where pore builder stripping and transformation of the precursor to active catalyst occur in separate operations with cooling of the precursor bodies between operations. Where the shaped precursor bodies are heated to a temperature of 240° C., for example, in stripping, they are exposed to potential dehydration not only during the plateau at 240° C. but also during the several hours typically required to cool to a temperature below about 150° C. Introduction of steam can be initiated at the beginning of the stripping cycle, if desired. However, the risk of excessive dehydration is not significant at temperatures below about 150° C. and particularly not below temperatures at which there is significant removal of pore builder. Thus, it is preferred that water vapor be incorporated throughout the portion of the stripping operation in which the temperature of the precursor bodies is above the temperature at which the vapor pressure of the pore builder is greater than 1 mm Hg.

It is important to achieve substantially complete removal of the pore builder before heat treatment of the precursor bodies to produce activated catalyst bodies. When exposed to oxygen during the heat treatment, residual pore builder may oxidize at an excessive rate, causing an excessive exotherm in that operation which may interfere with the conditions of the heat treatment. Thus, for example, when using the preferred method of activation as described below, it is important that the catalyst precursor bodies be heated in the presence of oxygen in the range of about 300° to about 400° C. at a rate no faster than about 2° to about 12° C. per minute. If any significant residual amount of pore builder is present, an exotherm may develop which increases the heating rate to well above 12° C. per minute. Accordingly, the removal step should be continued until at least 95% to 99.5% of the pore builder has been removed, as indicated, for example, by measured weight loss during the removal step.

Although 80 to 100% of the pore modification agent is advantageously removed by stripping with an inert purge gas, deleterious effects can also result if the catalyst body is exposed to a stream of inert gas at elevated temperature for too long a period of time. At temperatures above about 200° C., quantitative removal of a modestly volatile pore builder, such as stearic acid, may result in the further removal of oxygen from the crystal lattices of the precursor composition, with consequent reduction of vanadium. This result has been indicated by measured weight losses substantially in excess of 100% of the initial weight of pore builder when shaped bodies comprising the modified precursor composition have been "overstripped" by exposure to temperatures above 200° C. for extended periods of time. If the oxidation state of vanadium is reduced to a level of about 3.8 or less, as indicated, for example, by a weight loss of substantially greater than about 110% of the initial pore builder charge, the ultimate activity of the catalyst may be affected adversely and irreversibly. Moreover, if the oxidation state of the vanadium falls significantly below about 3.8, for example to the range of 3.6 or lower, as indicated by a weight loss of 110% to 150% or higher, re-oxidation of the vanadium during the subsequent activation step may cause an exotherm which also detracts from the ultimate activity of the catalyst. Moreover, exothermic re-oxidation may cause the formation of too high a concentration of pentavalent vanadium, so that the average oxidation state of the activated catalyst may fall above the desired 4.0 to 4.5 range.

In accordance with the invention, it has been discovered that the problem of vanadium reduction due to overstripping can be avoided in various ways. If the conditions of stripping are controlled to prevent a rapid rate of weight loss as the cumulative weight loss approaches 100%, and the stripping step is terminated before weight loss exceeds about 110%, preferably before it exceeds about 105%, complete removal of a volatile pore builder can be realized without significant reduction of vanadium. However, some modestly volatile pore builders may effect removal of lattice oxygens, at temperatures in which the oxygen atoms become labile, even before 100% of the pore builder has been removed. Stearic acid, for example, includes a carboxyl group which may bond very strongly to the substrate, resulting in abstraction of oxygen at temperatures above about 200° C. even when a significant residue of the pore builder is still present in the precursor body.

Where stearic acid or a comparable type of pore builder is used, the problem of oxygen abstraction and vanadium reduction may be prevented by including a modest proportion of oxygen or other oxidizing gas in the stripping gas during the final stages of stripping, at least from the point of 98% pore builder weight loss, more preferably from the point of about 95% pore builder weight loss. By maintaining the proportion of oxidizing gas low enough, specifically below the flammable range, residual pore builder may be eliminated by controlled oxidation without generating an excessive exotherm. If, for example, air is bled into the stripping gas so that it contains not greater than about 5%, preferably not greater than about 2%, by volume oxygen, residual fatty acid or similar organic pore builder can be entirely oxidized without generating an exotherm which increases the temperature of the catalyst bodies above 300° C. In fact, the oxygen concentration can be readily controlled, on a feed back control basis if desired, to maintain the temperature of the catalyst bodies below 275° or even 250° C. during the removal of residual pore builder. Moreover, if desired, a minor proportion of oxygen, such as about 1-3% by volume, may be incorporated in the stripping gas from any point in the stripping operation, even the very beginning, to effect quantitative removal of the pore builder without causing either an excessive exotherm during the removal process or reduction of vanadium below the desired oxidation state.

In fact, by use of controlled oxidation, even nonvolatile pore builders such as methyl cellulose may be effectively used without adverse effect on the final properties of the catalyst. According to the methods of the prior art, it was necessary to burn out such nonvolatile pore builders in a fashion which resulted in an excessive exotherm. More specifically, catalyst bodies containing cellulosic type pore builders were heated to rather elevated temperatures in the presence of air, causing decomposition of the pore builder into volatile fragments which were then burned in the air, causing the temperature of the catalyst body to rise far above 300° C., with consequently excessive and premature dehydration. However, by stripping with a dilute oxygen-containing gas under conditions below the flammable range, cellulosic pore builders can be entirely removed at temperatures substantially below 300° C. without excessive dehydration or other adverse effect on the precursor crystal lattice.

As indicated, brief temperature excursions as high as 350° C. may be tolerated if the energy absorbed by the precursor body is not such as to cause excessive dehydration during the removal step.

Alternatively, the pore builder comprises a relatively volatile compound such as naphthalene or other polynuclear organic which is free of polarity or functional groups that would generate high energy bonds with the precursor substrate. As noted, naphthalene offers the further advantage of a relatively low melting point, which results in melt flow to effectively carve out diffusion arteries within the catalyst body. Such a pore builder may be removed by stripping at temperatures, below about 175° C., at which the oxygen atoms of the precursor crystal lattice are essentially non-labile and the vanadium is not subject to reduction in its oxidation state. Enhanced removal of such pore builders may be achieved by operating under reduced pressure conditions, for example at a total pressure in the range of between about 150 and about 500 mm Hg. Vacuum stripping conditions may also be used to achieve removal fatty acid or other more tightly bonded pore building agents at temperatures low enough to avoid abstraction of oxygen and reduction of vanadium. Somewhat higher vacuums, for example total pressures in the range of between about 25 and about 250 mm Hg may be necessary to strip out fatty acid builders such as stearic, but total pressures in the range of between about 100 and about 500 mm Hg may be sufficient for effective removal of fatty acid monoesters.

Regardless of which of the above described methods is used, the pore builder is removed from the shaped porous body, leaving a porous, gas-permeable structure containing a substantial fraction of macropores, as discussed above. When the pore builder is removed by any of these methods, no substantial residue of carbon, ash or adsorbed organic species remains at the internal surfaces of the catalyst. Thus, when the precursor is subsequently transformed into active catalyst at temperatures in excess of 300° C., the highest feasible catalyst activity is realized. More particularly, the catalyst surfaces are not exposed to uncontrolled exothermic temperature excursions which may otherwise cause the temperature to rise more rapidly than about 2° to 12° C. per minute during the ramp heating from 300° to 400° C. as described in more detail hereinbelow.

Where a pore builder is burned out of a catalyst tablet by previously known methods, the internal surfaces are exposed to combustion temperatures, which are substantially in excess of the temperatures at which transformation of the catalyst precursor to active catalyst is effectively conducted. By contrast, in the process of the invention, the benefit of a substantial distribution of macropores is achieved, while the adverse effect of carbon deposits, physisorbed or chemisorbed organic species, or exposure of the pore surfaces to excessive temperatures, is avoided.

Where a relatively volatile pore builder is used, all or nearly all of it may be recovered without degradation (molecularly intact), and may be reused in the further production of porous catalyst bodies. The pore builder vapor that is expelled from the shaped bodies is condensed and collected in a receiver, from whence it can be transferred to the mixing operation in which particulate phosphorus/vanadium oxide catalyst precursor composition is mixed with pore builder to produce the modified precursor composition used in the process. Where the condensation temperature of the precursor is substantially above its melting point, the condensed pore builder is conveniently recovered and stored in liquid form for use in further processing operations. Optionally, the liquid pore builder composition may be formed into a powder of desired particle size by spraying from a nozzle into a cool gas stream in a powder spray chamber.

Figure 3:
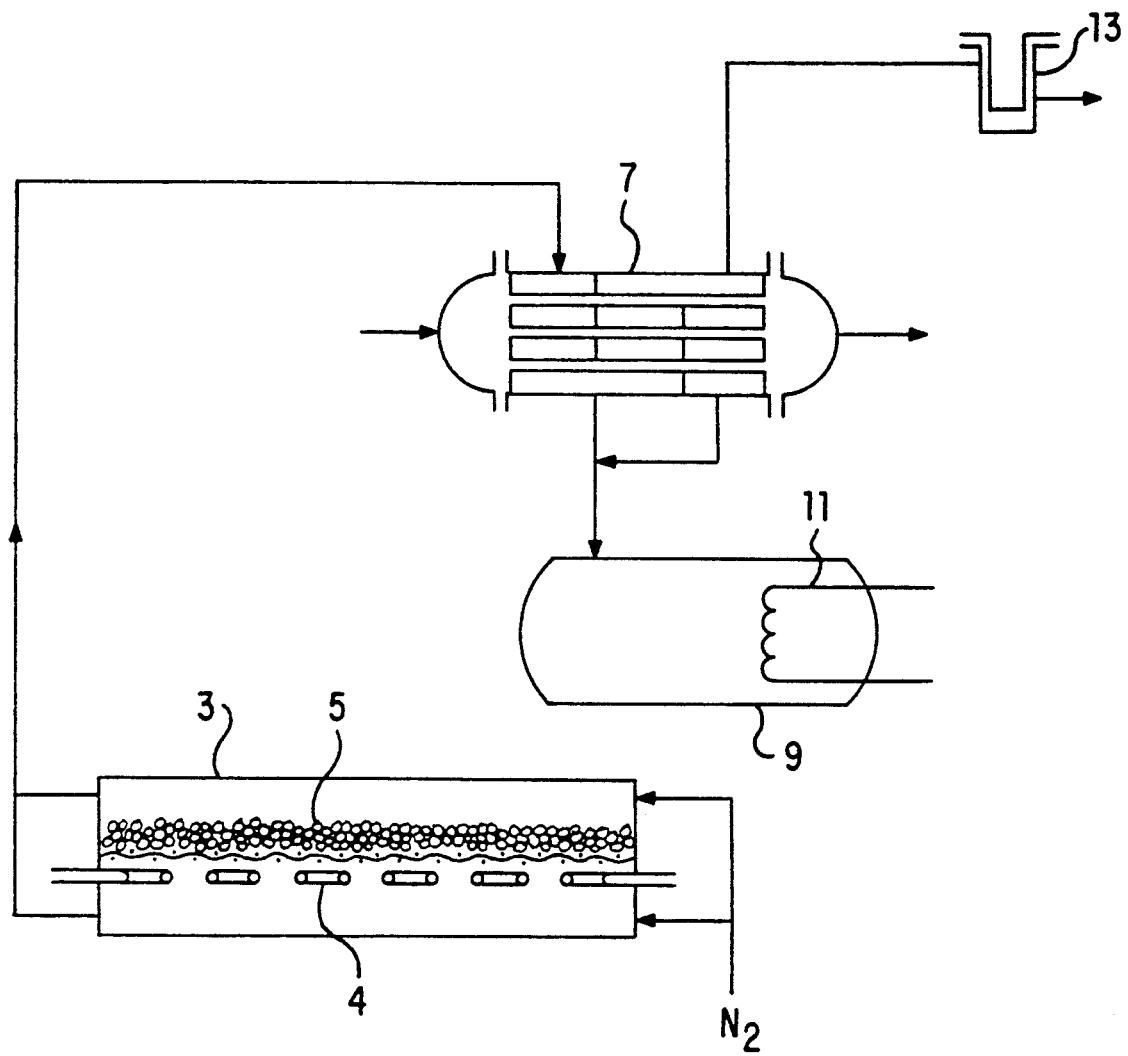
FIG. 3 is a schematic diagram showing an apparatus useful in the removal of a pore modification agent from a tabletted catalyst precursor composition and recovery of the pore modification agent for reuse.

A system for removal and intact recovery of a volatile pore builder is illustrated in FIG. 3. In the process shown, a stripping or purge gas is passed through a vessel containing a fixed bed 3 of shaped porous bodies 5 comprising the catalyst precursor composition containing the pore builder within their pores. A coil 4 under the catalyst bed provides a source of heat for removal of the builder. The stripping gas flows through the fixed bed at a space velocity in the range of between about 100 and about 1000 hr$^{-1}$ reduced to standard conditions of temperature and pressure. In a preferred embodiment, as illustrated, the gas flows both over and under a relatively thin, e.g., 1" thick bed. The pressure of the stripping gas and temperature of the shaped bodies falls within the ranges outlined above. Also as noted above, a small fraction of oxygen, below the flammable limit, may be incorporated to oxidize residual builder while preventing abstraction of labile oxygens and reduction of vanadium. The gas exiting the fixed bed passes out of the column to the shell side of a shell and tube condenser 7, where the pore builder stripped from the shaped bodies is condensed by indirect transfer of heat to water flowing through the tubes. Liquid pore builder drains from the condenser to a receiver 9, where it is maintained in the liquid state by a heating coil 11, and from which it can be withdrawn for reuse in the further preparation of the modified catalyst precursor composition. Stripping gas exiting the condenser passes through a cold finger 13 for recovery of residual pore builder from the gas stream.

After removal of the pore builder, the shaped catalyst body is subjected to calcination or other heat treatment to convert the catalyst precursor composition to active catalyst. Preferably, the transformation to active catalyst is carried out in the manner described in copending and coassigned application Ser. No. 7/722,070, now U.S. Pat. No. 5,137,860 which is expressly incorporated herein by reference. This application describes catalysts having a composition represented by the formula

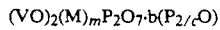

$(VO)_2(M)_m P_2O_7 \cdot b(P_{2/c}O)$ wherein M is at least one promoter element selected from among elements of Groups IA, IB, IIA, IIB, IIIA, IIIB, IVA, IVB, VA, VB, VIA, VIB, and VIIIA of the Periodic Table of the Elements, and mixtures thereof, m is a number from zero (0) to about 0.2, b is a number taken to provide a P/V atom ratio from about 1.0 to about 1.3, and c is a number representing the oxidation number of phosphorus and has a value of 5. The oxidation state of the vanadium is between about 4.0 and about 4.5, preferably between about 4.06 and about 4.30. The activated catalyst has a B.E.T. surface area of at least about 15 m$^2$/g, preferably at least about 20 m$^2$/g. By incorporating a substantial fraction of macropores, the activated catalyst provides avenues for access of reactant gases to the extensive active surface contained in what is also a high concentration of fine pores, and egress of product gases from the pores.

Although catalysts, as represented by the above formula, are indicated as having a phosphorus-to-vanadium (phosphorus/vanadium or P/V) atom ratio of from about 1.0 to about 1.3, preferably from about 1.0 to about 1.2, most preferably from about 1.05 to about 1.15, the actual P/V atom ratio may range from a value as low as about 0.9 up to the stated value of about 1.3. The total atom ratio of promoter element-to-vanadium (promoter element/vanadium or M/V), when a promoter element is present as a component of the catalyst, advantageously is in the range from about 0.0001 to about 0.2, preferably from about 0.0005 to about 0.1, most preferably from about 0.001 to about 0.05. These catalysts exhibit enhanced catalyst activity and excellent selectivities to and yields of maleic anhydride when compared to catalysts transformed from catalyst precursors via conventional procedures. Further enhancement of activity is provided by the use of a pore modification agent to produce high fractions of macropores as described above.

Catalyst precursors suitable for use in the process of the instant invention are those known in the art and in general are materials capable of being transformed in accordance with the process of the invention into active catalysts which are capable of catalyzing the vapor phase partial oxidation of non-aromatic hydrocarbons to maleic anhydride under oxidation conditions. Such catalyst precursors are represented by the formula

$VO(M)_m HPO_4 \cdot aH_2O \cdot b(P_{2/c}O) \cdot n(organics)$ wherein M, m, b, and c are as defined above, a is a number of at least about 0.5, and n is a number taken to represent the weight percent of intercalated or occluded organics component. The catalyst precursor may be prepared, for example, in an organic reaction medium such as primary and secondary alcohols--methanol, ethanol, 1-propanol, 2-propanol, 2-methyl-1-propanol (isobutyl alcohol), 3-methyl-2-butanol, 2,2-dimethyl-1-propanol, 1,2-ethanediol (ethylene gylcol), for example. Intercalated or occluded organic materials (organics), as represented by the term "n(organics)" in the formula for the catalyst precursors, may represent up to 40% by weight, or higher, typically from about 2% by weight to about 25% by weight, of the catalyst precursor composition, depending upon the conditions (temperature and time) under which the catalyst precursor is dried. For example, if the catalyst precursor is dried at about 150° C. for about 8 hours, the intercalated organic materials typically represent about 25% by weight, while drying at about 250° C. for about 4 hours typically results in a catalyst precursor having about 2% by weight intercalated organic materials. In general, the preparation of the catalyst precursors in an organic reaction medium is preferred over preparations carried out in an aqueous medium. Most preferred among suitable organic reaction media are the previously noted primary and secondary alcohols, with isobutyl alcohol being most preferred.

Specific, albeit nonlimiting, examples of suitable catalyst precursor materials are those described in U.S. Pat. Nos. 4,632,916; 4,632,915; 4,567,158; 4,333,853; 4,315,864; 4,328,162; 4,251,390; 4,187,235; 3,864,280; and European Patent Application No. 98,039—it being understood however, that the same are not to be construed as limiting but instead are for purposes of illustration and guidance in the practice of the process of the instant invention. These references are herein incorporated by reference. Among such catalyst precursor materials, nonlimiting examples of those preferred for use in the process of the instant invention are those described in U.S. Pat. Nos. 4,632,915 and 4,567,158.

In the process of the invention, a particulate catalyst precursor material is mixed with a pore modification agent to produce a modified catalyst precursor composition which is formed into a predetermined shape under compression. The catalyst precursor composition contained in this shaped body is transformed into an active catalyst by a series of steps conveniently referred to as calcination. This transformation, which is critical for the preparation of superior catalysts, is accomplished in three stages. For convenience, these may be referred to as (1) initial heat-up stage, (2) rapid heat-up stage, and (3) maintenance/finishing stage. Removal of the pore builder as described above may be carried out either prior to or as part of the initial heat-up stage of the calcination.

In the initial heat-up stage, the catalyst precursor is heated in an atmosphere selected from among air, steam, inert gas, and mixtures thereof, at any convenient heat-up rate to a temperature not to exceed the phase transformation initiation temperature which is about 300° C. In general, suitable temperatures for the initial heat-up stage range from about 200° to about 300° C. with a temperature from about 250° to about 275° C. being preferred.

If removal of pore builder occurs primarily during this initial heat-up stage, this step should be carried out under the conditions outlined above. If the pore builder has been substantially removed prior to the initial heat-up stage of the transformation to active catalyst, it may still be desirable to program the introduction of oxygen-containing gas during the heat-up in order to avoid the possible development of an excessive exotherm which might prematurely dehydrate the precursor or otherwise adversely affect the activated catalyst. The criteria for exothermic temperature excursions are essentially the same as for the pore builder removal stage, as described hereinabove. For this purpose, it is desirable that the oxygen content of the gas be maintained at not more than about 1.5%, preferably between about 0.1% and about 1.5% by volume during an initial heating period of between about 0.5 and about 10 hours, and not more than about 5%, preferably between about 2% and about 5%, by volume thereafter.

At temperatures above the temperature at which the vapor pressure of the pore builder is 1 mm Hg, the gas preferably contains at least about 5% by volume of water vapor.

After the desired temperature has been achieved in the initial heat-up stage, the initially selected atmosphere (in the event it does not contain molecular oxygen and steam and/or has a different composition than that which is desired for the rapid heat-up stage) is replaced by a molecular oxygen/steam-containing atmosphere, while maintaining the catalyst precursor at the temperature achieved in the initial heat-up stage. Such atmosphere optionally may contain an inert gas and, as such, may be conveniently represented by the formula

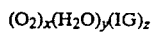

$(O_2)_x(H_2O)_y(IG)_z$ wherein IG is an inert gas and x, y, and z represent mol % (or volume %) of the $O_2$, $H_2O$, and IG components, respectively, in the molecular oxygen/steam-containing atmosphere, with x having a value greater than zero (0) mol %, but less than 100 mol %, y having a value greater than zero (0) mol %, but less than 100 mol %, and z having a value representing the balance of the molecular oxygen/steam-containing atmosphere. At least during the critical heating period, it is preferably at least about 5% by volume. A critical feature of the instant invention is that such atmosphere must contain at least a portion of molecular oxygen and water (as steam). The presence of the inert gas in such atmosphere, as indicated by the formula, is optional. Nonlimiting examples of suitable inert gases suitable for use in the molecular oxygen/steam-containing atmosphere include (molecular) nitrogen, helium, argon, and the like, with nitrogen generally being preferred for practical reasons.

Once the molecular oxygen/steam-containing atmosphere is provided, the catalyst precursor is subjected to the rapid heat-up stage of the calcination. In the rapid heat-up stage, the initial heat-up stage temperature is increased at a programmed rate of from about 2° C. per minute (° C./min) to about 12° C./min, preferably from about 4° C./min to about 8° C./min, to a value effective to eliminate or remove the water of hydration from the catalyst precursor. In general, a temperature of from about 340° C. to about 450° C., usually at least about 375° C. to about 425° C. is suitable. Because of the importance of controlling the rate of increase during this temperature ramp, it may be seen that a material should not be selected as a pore builder if it undergoes an exothermic decomposition or decomposes in any manner to flammable components at temperatures within the range of the ramp heating so that the rate of increase significantly exceeds about 12° C.

Following the rapid heat-up stage, the catalyst precursor is subjected to the maintenance/finishing stage of calcination. In the maintenance/finishing stage, the temperature, while maintaining the molecular oxygen/steam-containing atmosphere, is adjusted to a value greater than 350° C., but less than 550° C., preferably from about 375° C. to about 450° C., most preferably from about 400° C. to about 425° C. The adjusted temperature is then maintained, first in the molecular oxygen/steam-containing atmosphere for a time effective to provide a vanadium oxidation state of from about +4.0 to about +4.5 or simply from about 4.0 to about 4.5, and thereafter in a nonoxidizing, steam-containing atmosphere for a time effective to complete the catalyst precursor-to-active catalyst transformation to yield the active catalyst. In a manner similar to the molecular oxygen/steam-containing atmosphere, the nonoxidizing, steam-containing atmosphere also optionally may contain an inert gas, with nitrogen generally being the preferred inert gas for practical reasons.

The nonoxidizing, steam-containing atmosphere need not necessarily be completely free of molecular oxygen. However, such atmosphere preferably is substantially free of molecular oxygen. Accordingly, molecular oxygen may be present in an amount which is not effective to cause further oxidation of the vanadium beyond the desired oxidation state of about +4.0 to about +4.5, more particularly, not beyond the maximum desired oxidation state of about +4.5. In general, molecular oxygen may be present in amounts which do not exceed about 0.5 mol % of the nonoxidizing, steam-containing atmosphere.

It will be apparent to those skilled in the art that the period of time during which the adjusted temperature is maintained in the molecular oxygen/steam-containing atmosphere in order to provide the desired vanadium oxidation state of from about +4.0 to about +4.5 will depend to some extent upon the vanadium oxidation state achieved during the rapid heat-up stage, which, in turn, will depend to some extent upon the period of time during which the catalyst precursor material is exposed to the molecular oxygen/steam-containing atmosphere at the stated rapid heat-up stage temperatures. In general, a period of time of from about 0.25 hour to about 2 hours is suitable, with a period of time of from about 0.5 hour to about 1 hour being preferred.

A suitable period of time during which the adjusted temperature is maintained in the nonoxidizing, steam-containing atmosphere is at least 1 hour, although longer periods of time up to 24 hours, or longer, may be employed, if desired, with a period of time of from about 3 hours to about 10 hours being preferred, and a period of about 6 hours being most preferred.

Catalysts of the present invention have been demonstrated to afford enhanced yields in the range of 2-4% higher than otherwise comparable catalysts that have not been processed to provide the proportions of macropores described hereinabove. The catalysts of the invention are also superior to catalysts which contain a similar proportion of macropores, but have been prepared by burning a pore builder out of a catalyst precursor tablet or pellet under conditions which expose the catalyst body to a substantial exotherm. Careful removal of the pore builder under mild conditions avoids the deposit of carbon on the active surfaces of the catalyst pores or abstraction of labile oxygens and reduction of the vanadium oxidation state, and further avoids interference with the critical chemistry by which the precursor is transformed to high surface area active catalyst under the controlled heating conditions described above. Moreover, by substantially recovering the pore builder molecularly intact for reuse, the process of the invention avoids the discharge of organic vapors or combustion products into the atmosphere. A savings in the consumption of pore builder is also realized.

FIGS. 6–13 are photomicrographs showing the external surface of a catalyst tablet of the invention. Distributed over the surface of this tablet are exit holes through which the pore builder has escaped during the process of its removal. By removal of the pore builder under mild conditions, a distribution is obtained in which the exit holes greater than about 2 microns in diameter have a density of at least about $100/mm^2$, more preferably at least about $200/mm^2$ on the external surfaces of the catalyst bodies. These holes are in communication with the interior of the body and further facilitate the ingress of reactant gases and egress of product gases.

The following examples illustrate the invention.

EXAMPLE 1

A 12-liter, round bottom flask, fitted with a paddle stirrer, a thermometer, a heating mantle, and a reflux condenser, was charged with 9000 ml of isobutyl alcohol, 378.3 grams (4.20 mols) of oxalic acid, and 848.4 grams (4.66 mols) of $V_2O_5$ to which was added 997.6 grams (10.76 mols of $H_3PO_4$ (105.7%)). The resulting mixture was then refluxed for about 16 hours to give a bright blue mixture. After stripping off 25% of the alcohol solvent (2.2 L), the mixture was cooled and 50% of the remaining isobutyl alcohol was decanted away to produce a concentrated slurry, and then the slurry was quantitatively transferred to a flat dish and dried between 110° C. and 150° C. for 24 hours in nitrogen. The dried material was then further dried by heating in air at 250°-260° C. for several hours to yield a grey-black catalyst precursor powder.

The catalyst precursor prepared in this manner was then divided into separate portions and each portion separately processed to produce active catalyst. Blends were produced containing 2 to 12 wt % of a fatty acid mixture (composition of a fatty acid mixture in % by weight-palmitic [50%]; stearic acid [45.5%]; myristic acid [4.5%] having a melting point of 54.5° to 55.5° C. and a boiling point of 386° C. at 760 mm mercury and a mean particle diameter of 224 microns) and the precursor powder. The blends were individually made into 12.7 mm diameter cylinderical slugs with a table density of 1.3 to 1.4 g/cc using a Stokes 512 Rotary Tableting machine. These slugs were granulated to less than 1 mm particles to produce the dense powder which was tabletted into 6.35 mm diameter cylinders having three equidistant spaced grooves etched in the longitudinal surface thereof (57% geometric volume of the corresponding solid cylinder). A similar procedure was used to prepare 6.35 mm diameter tablets containing 4 wt % graphite and 0 wt % fatty acid mixture. The 6.35 mm diameter tablets with 15 wt % fatty acid were prepared from a blend of the catalyst powder slugged with 4 wt % graphite to which was added 15% by weight fatty acid.

The catalyst systems were then treated as follows: About 15-20 gms of catalyst tablets (with 2 to 12 wt % fatty acid mixture) were placed into a box oven purged with nitrogen gas and heated to approximately 240° C., and held for one hour. The atmosphere in the oven was changed to 50 volume percent nitrogen and 50 volume percent steam, and air was incremented in three steps over $\approx 60$ minutes to give a gas composition of [25:25:50] volume per cent [air:nitrogen:steam]. The temperature was maintained at 240° C. in this atmosphere for $\approx 60$ minutes. Next, the temperature was raised at a controlled rate of 4° C./min to $\approx 425$° C. and held there for $\approx 1$ hour, at which point the atmosphere in the oven was changed to 50 volume percent nitrogen and 50 volume percent steam and maintained at 425° C. for 6 hours. The tray of catalyst structures was then allowed to cool to room temperature while purging the oven with dry nitrogen.

Also, 15-20 gms of catalyst tablets (with 0 and 15 wt % fatty acid mixture) were placed into a box oven purged with nitrogen gas and heated to approximately 180° C., then heated to 240° C. at 4° C./min in a 40 liter/min 50:50 mixture of air:nitrogen, and held at 240° C. for 90 minutes. Next, the atmosphere in the oven was changed to a mixture of 50 volume percent air and 50 volume % steam, and the temperature was raised at a controlled rate of 4° C./min to $\approx 425$° C. and held there for $\approx 1$ hour. The atmosphere in the oven was changed to 50 volume percent nitrogen and 50 volume percent steam and maintained at $\approx 425$° C. for 6 hours. The tray of catalyst structures was then allowed to cool to room temperature while purging the oven with dry nitrogen. The thusly prepared catalyst bodies were performance tested as described in Example 4 below.

The densities and side crush strengths of the tablets were measured before (formed) and after activation (activation is defined as heating with oven temperatures > 300° C.). For the activated catalyst of this example, the total pore volume and pore size distribution was determined by mercury porosimetry, the vanadium oxidation state was determined by chemical titration, and surface area by the BET method. The data so obtained is set forth in Table 1A and 1B.

The total pore volume and pore size distribution of each of the catalyst of this example was determined by mercury porosimetry. The tablet density of the catalyst structure and the crush strength of the catalyst structure both before and after activation by ANST were also determined. The data so obtained are set forth in Table 1.

per cent [air:nitrogen:steam]. The temperature was maintained at 240° C. in this atmosphere for ≈60 minutes. Next, the temperature was raised at a controlled rate of 4° C./min to ≈425° C. and held there for ≈1 hour, at which point the atmosphere in the oven was changed to 50 volume percent nitrogen and 50 volume percent steam and maintained at ≈425° C. for 6 hours. The tray of catalyst structures was then allowed to cool to room temperature while purging the oven with dry

TABLE 1A

| CATALYST NO. | WT % PMA[c] | SIDE CRUSH LBS FORMED | SIDE CRUSH LBS ACT | TAB DENS FORMED | G/CC ACT | ACT Vox | ACT SA.m2/gm |
|---|---|---|---|---|---|---|---|
| I | 0 | 9 | 10 | 1.75 | 1.55 | 4.15 | 23 |
| II | 2 | 12 | 10 | 1.92 | 1.75 | 4.13 | 24 |
| III | 2 | 22 | 9.6 | 2.13 | 1.88 | 4.11 | 23.8 |
| IV | 4 | 10 | 9.9 | 1.92 | 1.71 | 4.14 | 25.5 |
| V | 4 | 15 | 8.4 | 2.03 | 1.79 | 4.14 | 24.8 |
| VI | 8 | 9 | 8.7 | 1.81 | 1.53 | 4.15 | 22.3 |
| VII | 8 | 14 | 10.2 | 2.07 | 1.78 | 4.15 | 21 |
| VIII | 12 | 8 | 7 | 1.89 | 1.53 | 4.14 | 22.4 |
| IX | 15 | 8 | 4.3 | 1.63 | 1.25 | NA | 23.7 |

TABLE 1B

| CATALYST NO. | WT % PMA | PORE VOL[a] CC/GM | PORE VOL. >10μ CC/G | PORE VOL. >.8μ CC/G | % PORES >10μ | % PORES >0.8μ | PV(10 − .8μ) | # of >2μ Pores Per mm2 [b] |
|---|---|---|---|---|---|---|---|---|
| I | 0 | 0.275 | 0.0035 | 0.0041 | 1.3 | 1.5 | 0.0006 | 0 |
| II | 2 | 0.194 | 0.0043 | 0.0057 | 2.2 | 2.9 | 0.0014 | 42 |
| III | 2 | 0.16 | 0.0037 | 0.0052 | 2.3 | 3.3 | 0.0015 | NA |
| IV | 4 | 0.209 | 0.0042 | 0.0059 | 2.0 | 2.8 | 0.0017 | 58 |
| V | 4 | 0.176 | 0.0055 | 0.0095 | 3.1 | 5.4 | 0.0040 | 75 |
| VI | 8 | 0.267 | 0.0109 | 0.0249 | 4.0 | 9.3 | 0.0141 | 300 |
| VII | 8 | 0.188 | 0.0128 | 0.0408 | 6.8 | 21.7 | 0.0280 | 275 |
| VIII | 12 | 0.268 | 0.0315 | 0.0717 | 11.8 | 26.8 | 0.0402 | 825 |
| IX | 15 | 0.323 | 0.1092 | 0.1338 | 33.8 | 41.4 | 0.0246 | 1250 |

[a]The pore volumes were determined by mercury porosimetry, and the pore diameters are the mean pore size.
[b]The number of pores at the external surface of the particle were estimated using the optical microscope to magnify the external surface of three lobes of the tablet by ≈250 times, counting the pores >2μ in each of three 200 × 200 micron areas, and averaging the results.
[c]mixed fatty acid pore modification agent

EXAMPLE 2

Using the method described in Example 1, activated catalysts were prepared in the form of 3.97 mm diameter cylinders having three equidistant spaced grooves etched in the longitudinal surface thereof (60.6% geometric volume of the corresponding solid cylinder). A control sample was prepared in which graphite (4% by weight) was used as a lubricant and no pore builder was included in the formulation. Other catalysts were prepared from modified catalyst precursor containing between 2 and 15% by weight fatty acid mixture. The catalyst systems were treated as follows: About 15-20 gms of catalyst tablets (with 2 to 15 wt % fatty acid mixture) were placed into a box oven purged with nitrogen gas and heated to approximately 240° C., and held for one hour. The atmosphere in the oven was changed to 50 volume percent nitrogen and 50 volume percent steam, and air was incremented in three steps over ≈60 minutes to give a gas composition of [25:25:50] volume nitrogen. The thusly prepared catalyst bodies were performance tested as described in Example 4 below.

The densities and side crush strengths of the tablets were measured before (formed) and after activation (activation is defined as heating with oven temperatures >300° C.). For the activated catalyst of this example, the total pore volume and pore size distribution was determined by mercury porosimetry. The data so obtained is set forth in Table 1A and 1B.

TABLE 2A

| CATALYST NO. | WT % PMA | SIDE CRUSH LBS FORMED | SIDE CRUSH LBS ACT | TAB DENS G/CC FORMED | TAB DENS G/CC ACT |
|---|---|---|---|---|---|
| X | 0 | 9 | 10 | 1.75 | 1.55 |
| XI | 2 | NA | 18 | NA | 1.87 |
| XII | 4 | 19 | 9 | 1.88 | 1.74 |
| XIII | 8 | 16 | 17 | 2.01 | 1.81 |
| XIV | 8 | 9 | 9 | 1.78 | 1.54 |
| XV | 12 | 6 | 5 | 1.80 | 1.46 |
| XVI | 15 | 6 | <1 | 1.72 | 1.20 |

TABLE 2B

| CAT. NO. | WT % Fat. Acid | TOTAL PORE VOLUME CC/GM | PORE DISTRIBUTION >10μ CC/G | PORE DISTRIBUTION >0.8μ CC/G | PORES >10μ | PORES >0.8μ | PV(10 − .8μ) CC/G |
|---|---|---|---|---|---|---|---|
| X | 0 | NA | NA | NA | NA | NA | NA |
| XI | 2 | 0.2281 | 0.009 | 0.0133 | 3.95 | 5.83 | 0.0043 |
| XII | 4 | 0.2718 | 0.005 | 0.0066 | 1.99 | 2.43 | 0.0012 |

TABLE 2B-continued

| CAT. NO. | WT % Fat. Acid | TOTAL PORE VOLUME CC/GM | PORE DISTRIBUTION >10μ CC/G | >0.8μ CC/G | PORES >10μ | PORES >0.8μ | PV(10 − .8μ) CC/G |
|---|---|---|---|---|---|---|---|
| XIII | 8 | 0.2676 | 0.019 | 0.0337 | 7.06 | 12.59 | 0.0148 |
| XIV | 8 | 0.2913 | 0.096 | 0.1175 | 33.02 | 40.34 | 0.0213 |
| XV | 12 | 0.3581 | 0.141 | 0.1604 | 39.43 | 44.79 | 0.0192 |
| XVI | 15 | 0.45 | 0.268 | 0.2995 | 59.51 | 66.56 | 0.0317 |

EXAMPLE 3

A five liter, round bottom flask, fitted with a paddle stirrer, a thermometer, a heating mantle and a reflux condenser was charged with 3400 ml of isobutyl alcohol, 141.9 grams of oxalic acid, and 318.3 grams of $V_2O_5$ to which was added 373.2 grams of $H_3PO_4$ (105.7%). The resulting mixture was then refluxed for 5 hours to give a bright blue mixture, cooled to 30°–70° C., and then zirconium was added as 32.05 gms $Zr(C_4H_9O)_4 \cdot C_4H_9OH$ solution with $\approx 200$ ml isobutyl alcohol. Heat again to reflux and hold for an additional five hours. After cooling to room temperature, the blue solid is separated by vacuum filtration, and dried between 110° C. and 150° C. in a nitrogen purged vacuum oven (at an absolute pressure of 150 mm Hg).

Portions of the catalyst precursor powder were treated in the following fashion: About 105 gms of the individual powder was loaded into a 1" OD stainless steel tube with ⅛" centered thermocouple well, and the powder was fluidized with about 900 cc STP/min nitrogen gas. The powder bed temperature was raised to 260° C. and held for one hour at which time a 50:50 steam:air mixture was introduced incrementally such that the powder was treated with 1.32% oxygen for 20 minutes, 2.625% oxygen for 20 minutes, 5.25% oxygen for 20 minutes, 10.5% oxygen for 60 minutes, and then 100% nitrogen during the cool down to room temperature.

The precursor powder prepared in this manner has stoichiometry of $\approx Zr_{0.02}[VOHPO_4] \cdot 0.5\ H_2O \cdot 0.15(P_4O)$ Using powder produced as above, a blend was produced containing 15 wt % of a fatty acid mixture (composition of a fatty acid mixture in % by weight-palmitic [50%]; stearic acid [45.5%]; myristic acid [4.5%]) and catalyst powder. The blend was made into 12.7 mm diameter cylinders with a tablet density of 1.3 to 1.4 g/cc using a Stokes 512 Rotary Tableting machine. These slugs were granulated to less than 1 mm particles to produce the dense powder which was tableted into 6.35 mm diameter cylinders having three equidistant spaced grooves etched in the longitudinal surface thereof (57% geometric volume of the corresponding solid cylinder). A similar procedure was used to prepare tablets containing 4 wt % graphite and 0 wt % fatty acid mixture.

Figure 4:
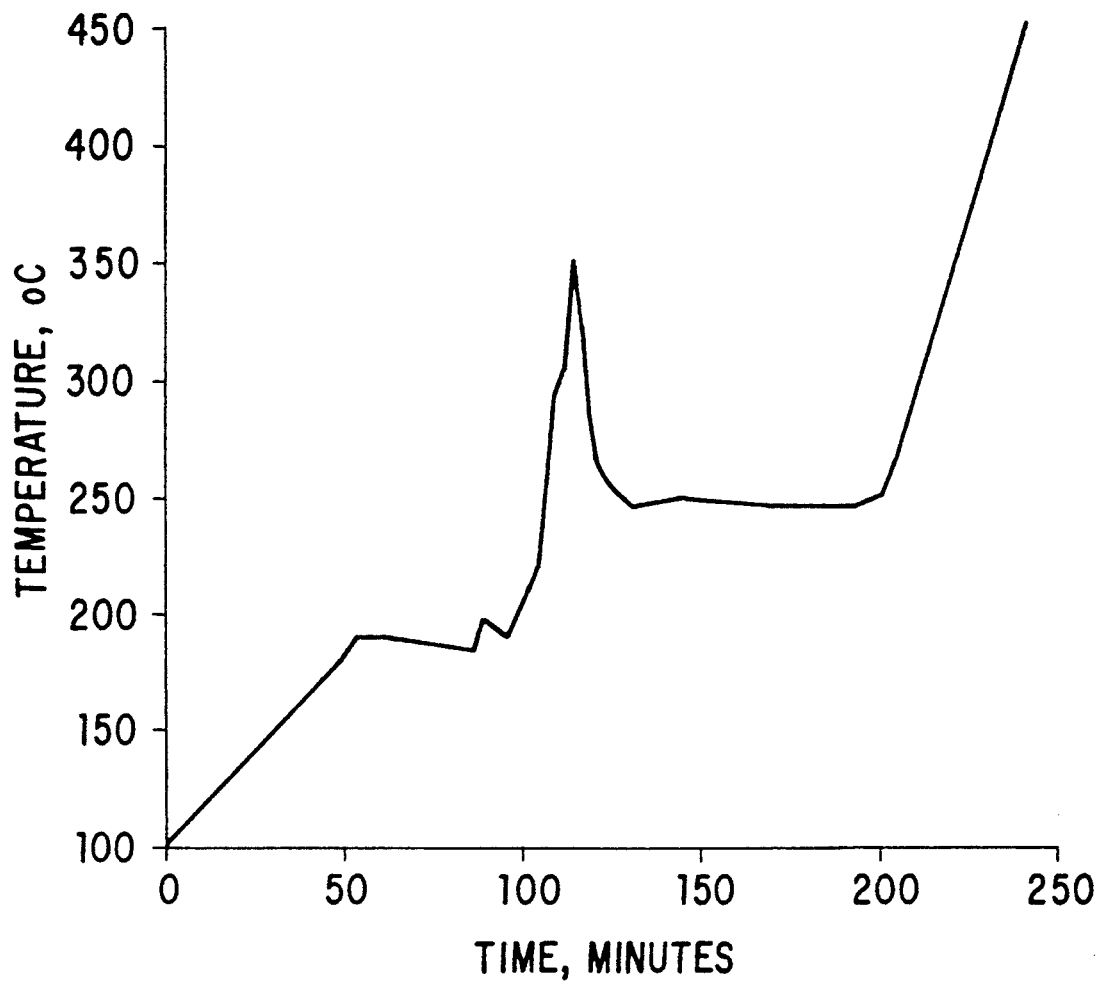
FIG. 4 is a copy of a temperature recording chart illustrating an excessive exotherm in the removal of pore builder, which resulted in the formation of a catalyst having less than desired activity.

The catalyst systems were then treated as follows:

PROCEDURE 3A About 15-20 gms of catalyst tablets (with and without mixed fatty acid pore builder) were placed into a box oven purged with nitrogen gas and heated to approximately 180° C., held at that temperature for about 40 minutes then heated to 240° C. at 4° C./min in a 40 liter/min 50:50 mixture of air:nitrogen, and held at 240° C. for 90 minutes. A large exotherm occurred in the fatty acid containing sample during this step, as shown in FIG. 4. Next, the atmosphere in the oven was changed to a mixture of 50 volume percent air and 50 volume % steam, and the temperature was raised at a controlled rate of 4° C./min to $\approx 425°$ C. and held there for $\approx 1$ hour. The atmosphere in the oven was changed to 50 volume percent nitrogen and 50 volume percent steam and maintained at $\approx 425°$ C. for 6 hours. The tray of catalyst structures was then allowed to cool to room temperature while purging the oven with dry nitrogen.

Figure 5:
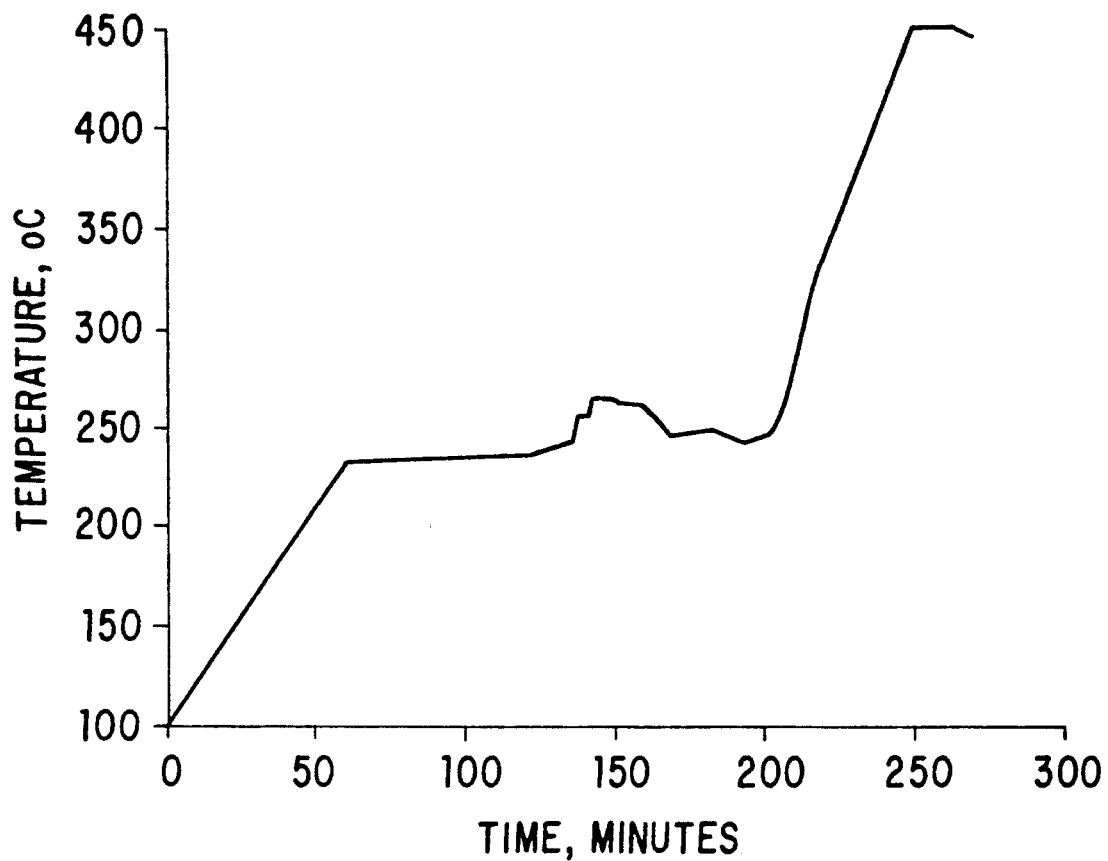
FIG. 5 is a copy of a temperature recording chart illustrating a tolerable temperature excursion in removal of pore modification agent in accordance with the process of the invention.
Figure 6A:
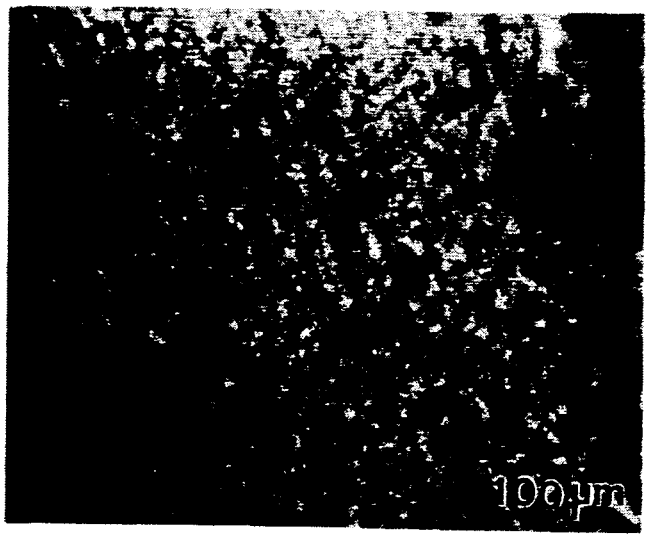
FIGS. 6 to 13, each figure containing figures a, b and c, are external photomicrographs of a catalyst tablet of the invention showing the incidence of surface holes communicating with the interior of the tablet.
Figure 6B:
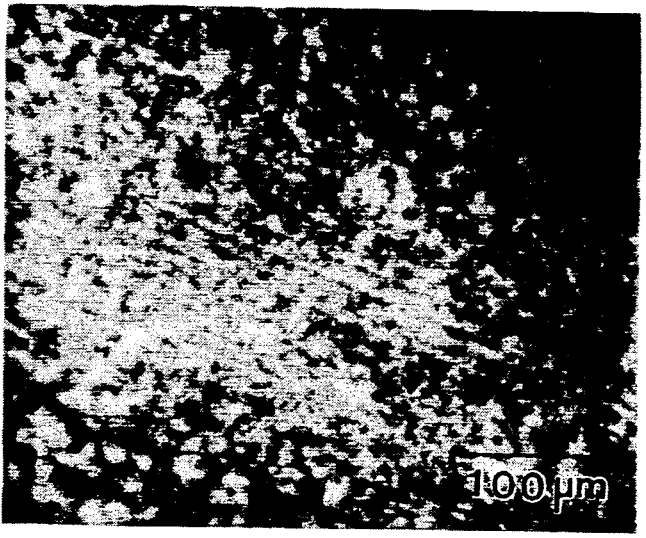
Figure 6C:
Figure 7A:
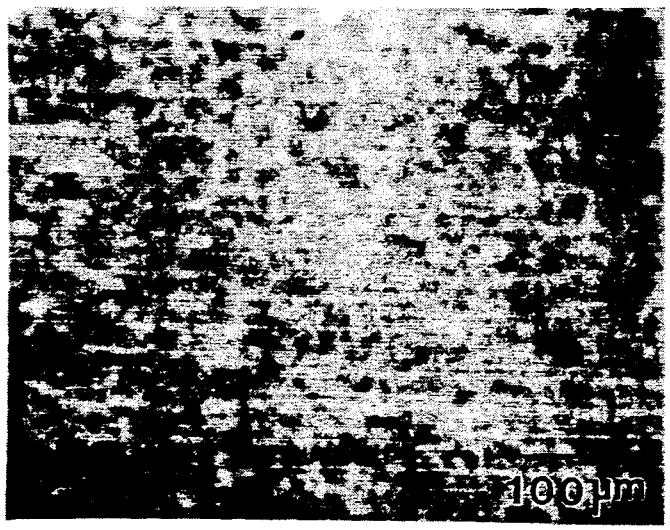
Figure 7B:
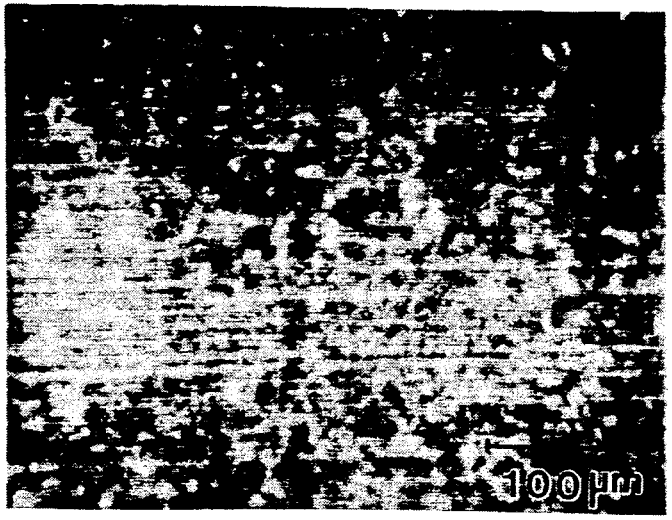
Figure 7C:
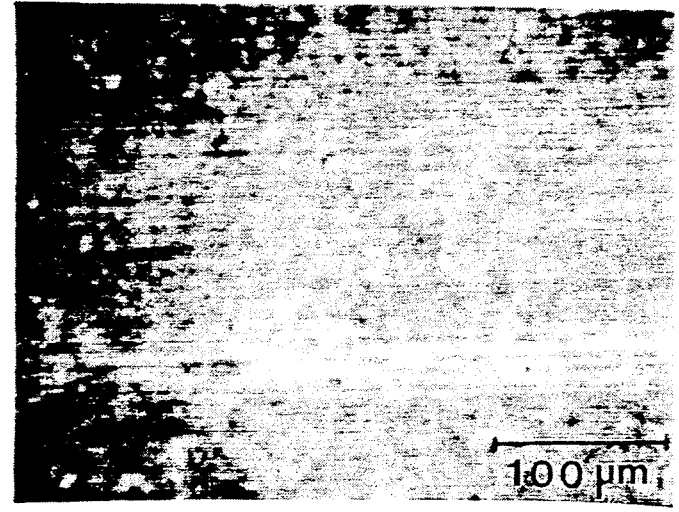
Figure 8A:
Figure 8B:
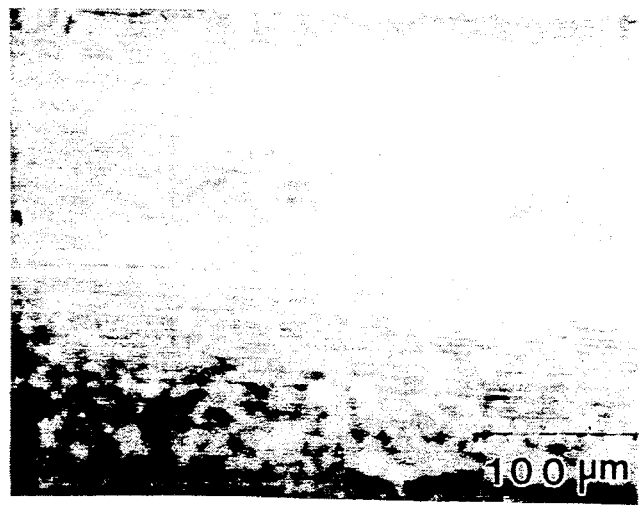
Figure 8C:
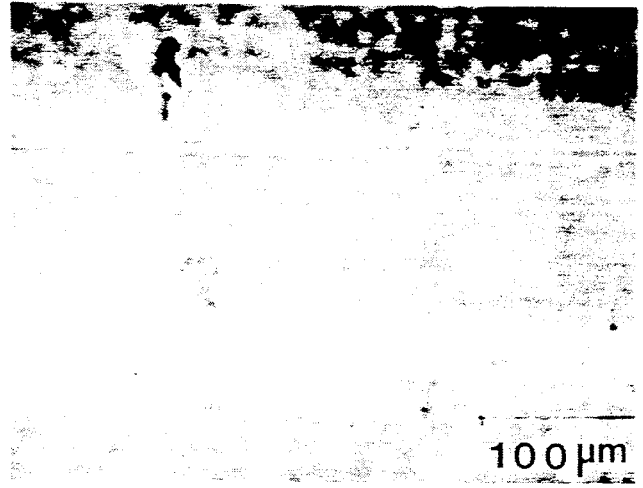
Figure 9A:
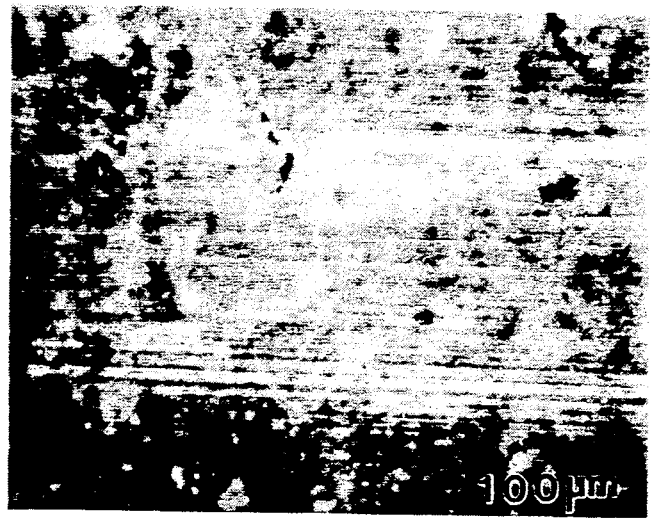
Figure 9B:
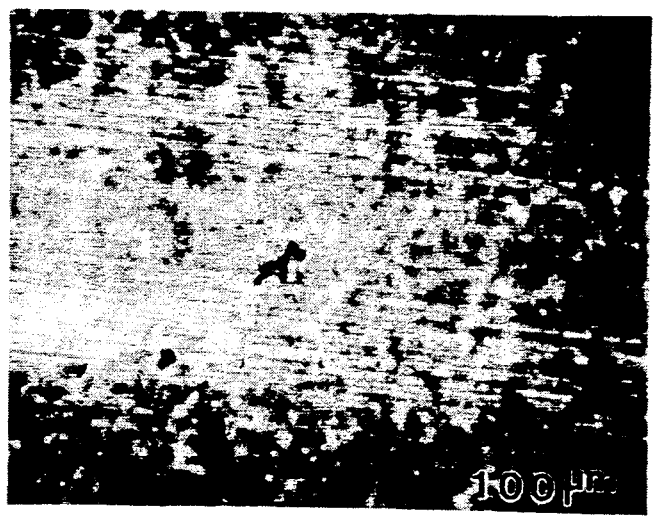
Figure 9C:
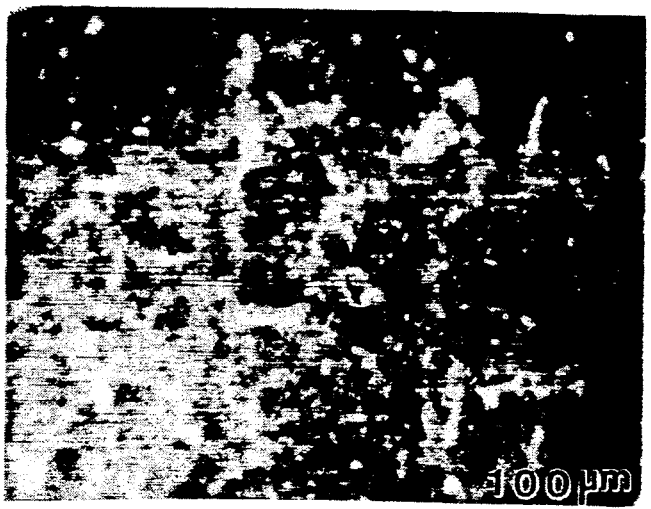
Figure 10A:
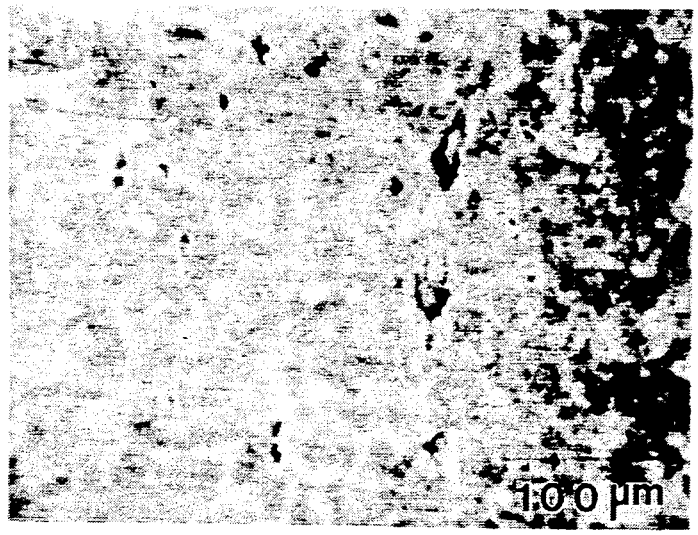
Figure 10B:
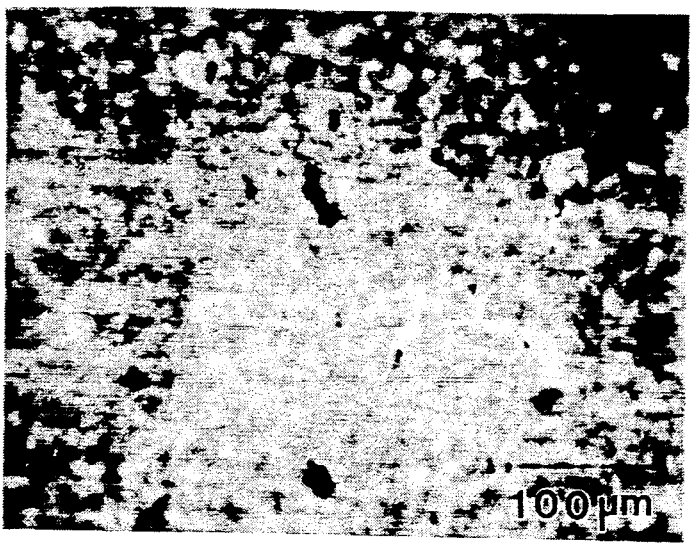
Figure 10C:
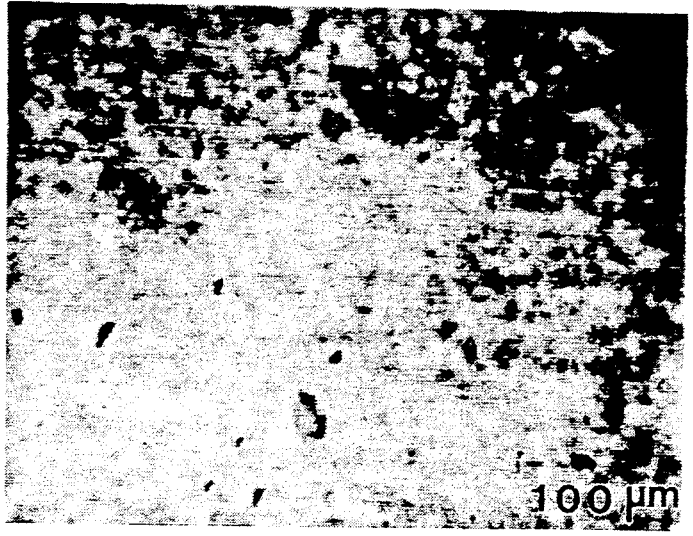
Figure 11A:
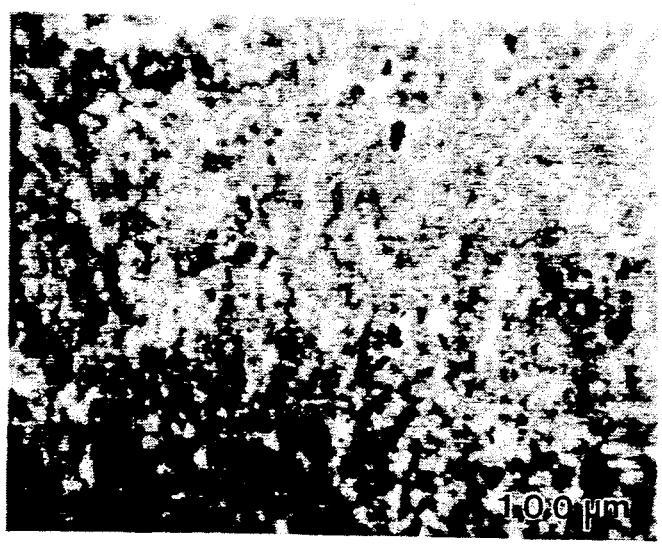
Figure 11B:
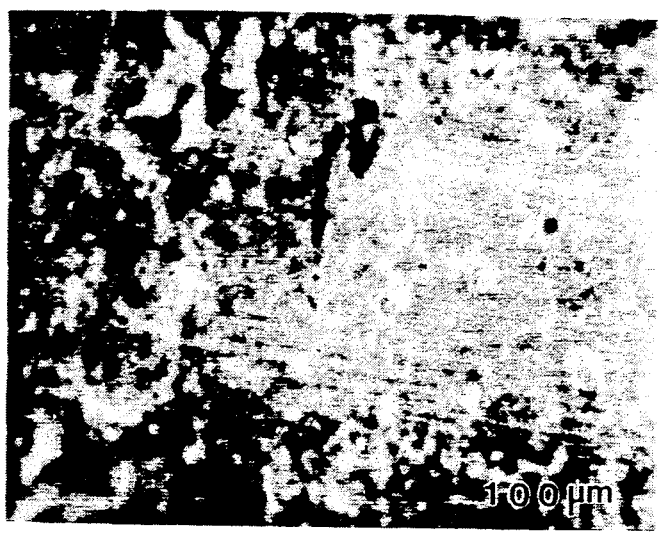
Figure 11C:
Figure 12A:
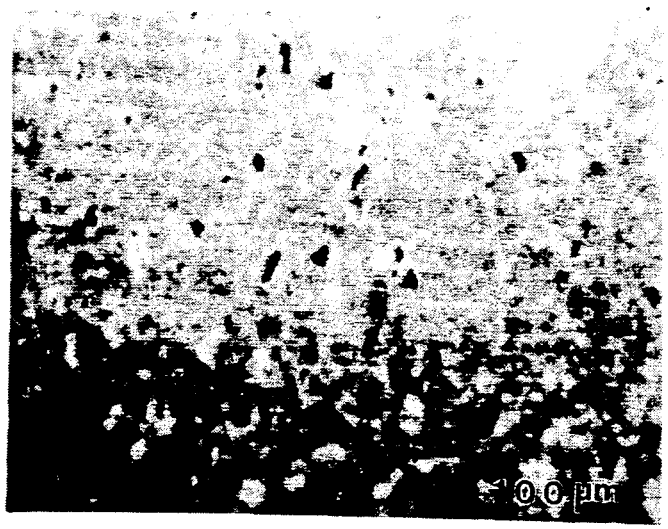
Figure 12B:
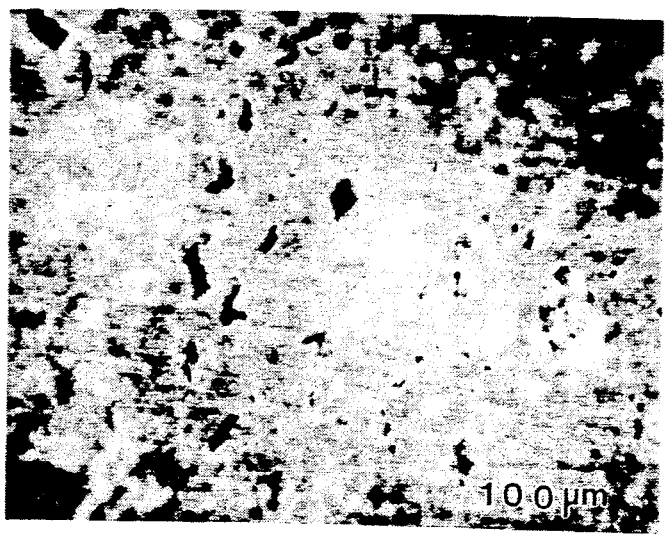
Figure 12C:
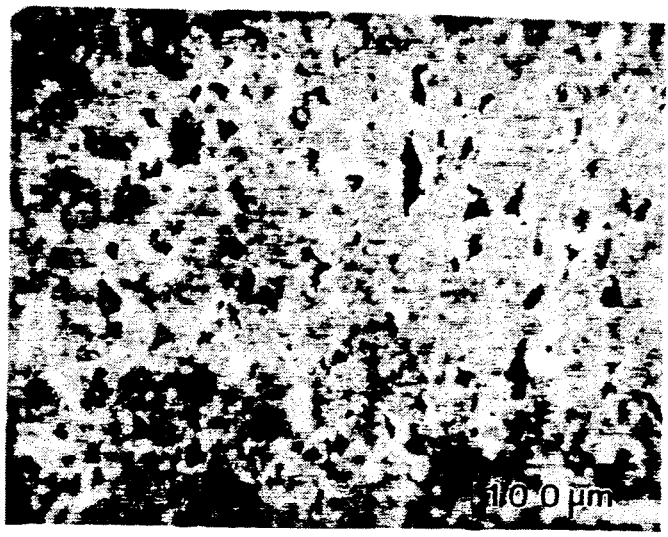
Figure 13A:
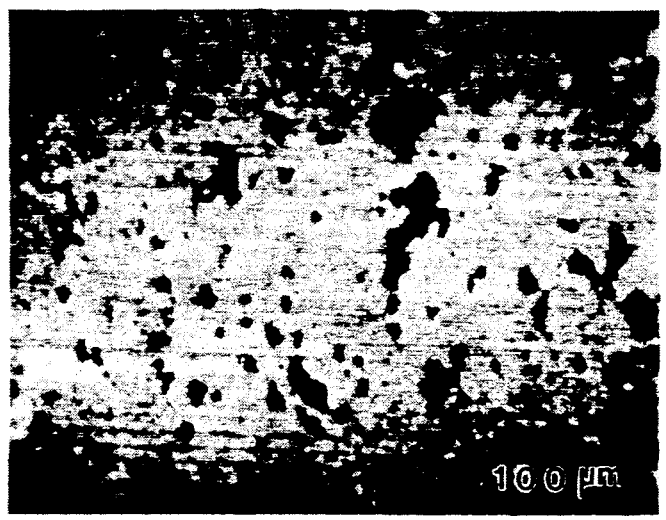
Figure 13B:
Figure 13C:
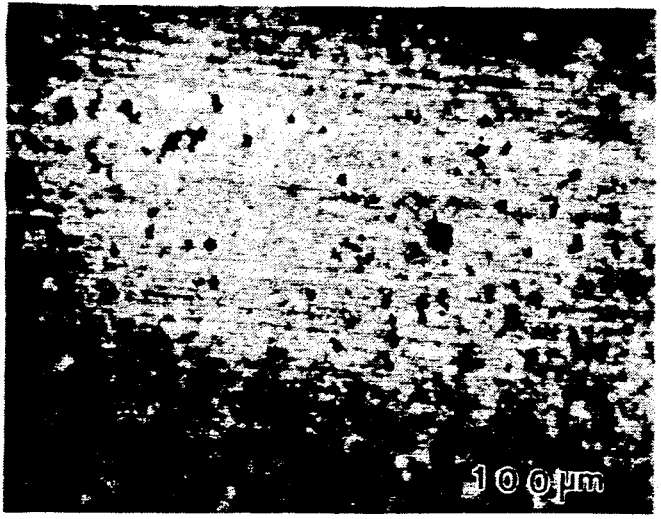

PROCEDURE 3B About 15-20 gms of catalyst tablets (with and without mixed fatty acid pore builder) were placed into a box oven purged with nitrogen gas and heated to approximately 240° C., held for one hour, and then the atmosphere in the oven was changed to 50 volume percent nitrogen and 50 volume percent steam. Air was then incremented in three steps over $\approx 60$ minutes to give a gas composition of 25:25:50 volume percent air:nitrogen:steam, and then held at 240° C. for $\approx 60$ minutes. The large exotherm observed in PROCEDURE 3A was avoided, as shown in FIG. 5. Next, the temperature was raised at a controlled rate of 4° C./min. to $\approx 425°$ C. and held there for $\approx 1$ hour, then the atmosphere in the oven was changed to 50 volume percent nitrogen and 50 volume percent steam and maintained at $\approx 425°$ C. for 6 hours. The tray of catalyst structures was then allowed to cool to room temperature while purging the oven with dry nitrogen. The thusly prepared catalyst bodies were performance tested as described in Example 4 below.

The densities and side crush strengths of the tablets were measured before (formed) and after activation (activation is defined as heating with oven temperatures greater than 300° C.). For the activated catalyst of this example, the total pore volume and pore size distribution was determined by mercury porosimetry. The data so obtained is set forth in Table 3A.

TABLE 3A

| | CATALYST NUMBER | | |
|---|---|---|---|
| | XVII | XVIII | XIX |
| WT % ACID ACT | 15(3B) | 15(3A) | 0(3A) |
| PORE VOLUME CC/GM | 0.28 | 0.258 | 0.238 |
| PORE VOLUME >10μ CC/G | 0.022 | 0.023 | 0.004 |
| PORE VOLUME >.8μ CC/G | 0.069 | 0.073 | 0.004 |
| % PORES >10μ | 7.8 | 8.9 | 1.7 |
| % PORES >0.8μ | 24.6 | 28.3 | 1.7 |
| PV(10 − .8μ) | 0.0472 | 0.05 | 0 |
| CRUSH LBS FOR. | 8 | 8 | 8 |
| CRUSH LBS ACT | 3 | 3 | 8 |
| TAB DENS FOR. | NA | 1.75 | 1.63 |
| TAB DENS ACT | NA | 1.3 | 1.52 |

EXAMPLE 4

Each of the catalyst prepared in accordance with Examples 1 through 3 was performance tested at a standardized set of reaction conditions—2.4±0.2 mol % in n-butane in synthetic air (21 mol % oxygen/71 mol % helium), $1.034 \times 10^2$ kPa-g (15.0 psig) inlet pressure, and 1,500 GHSV. The catalyst (12.0 g) was charged to a 1.092 cm inside diameter×30.48 cm long (0.43 inch inside diameter by 1' long) reactor to provide a catalyst bed of approximately 15.24 cm (6") in length. The catalyst was run for a period of time from about 20 hours to about 100 hours unless otherwise indicated at the standardized performance test conditions prior to determining the reaction (bath) temperature and reaction yield. The reaction (bath) temperature and maximum yield were determined for each catalyst when the catalyst was running at 85±2 mol % n-butane conversion. The parameters and results are tabulated in Table 4.

TABLE 4

| CATALYST NO. | EXAMPLE # | WT % FATTY ACID | CATALYST PERFORMANCE[1] | |
|---|---|---|---|---|
| | | | % BCY | BATH, T |
| I | 2 | 0 | 54.5 | 414 |
| II | 2 | 2 | 52.6 | 423 |
| III | 2 | 2 | | |
| IV | 2 | 4 | 52.6 | 420 |
| V | 2 | 4 | 53.6 | 419 |
| VI | 2 | 8 | 57.0 | 410 |
| VII | 2 | 8 | 56.7 | 412 |
| VIII | 2 | 12 | 57.2 | 410 |
| IX | 2 | 15 | 58.1 | 414 |
| X | 3 | 0 | 57.5 | 408 |
| XI | 3 | 2 | 57.0 | 406 |
| XII | 3 | 4 | 57.5 | 404 |
| XIII | 3 | 8 | 58.0 | 398 |
| XIV | 3 | 8 | 59.0 | 398 |
| XV | 3 | 12 | 60.0 | 395 |
| XVI | 3 | 15 | 60.0 | 396 |
| XVII | 3 | 15 | 58.8 | 399 |
| XVIII | 3 | 15 | 58.6 | 412 |
| XIX | 3 | 0 | 55.5 | 420 |

[1] % BCY (% Back Calculated Maleic Yield) and Bath Activity Temperature (°C. required to give 85 ± 1% butane conversion) were obtained from microreactors running at 1500 GHSV, 15 psig, and mole 2.4% butane.

EXAMPLE 5

Overstripping of VPO Catalyst (3434149 and 4972362)

The catalyst precursor powder in Example 1 was dry blended with 10 wt. % of a fatty acid mixture having a mean particle size of 69 microns. The blend was formed into slugs, ground to less than 1 mm powder, then tableted into the 6.35 mm shapes described in Example 1. The shaped tablets, 649.2 g, were loaded into a 16-mesh stainless steel cylinder that was 2.35 inches o.d. and 16.125 inches in length. The filled cylinder was lowered into a vertically hung tube that was heated evenly about the tube shell. The tablets were heated to 240° C. for about 20 hrs. with a 6 liters/min purge of nitrogen gas. The tablets were recovered and found to weigh 547.0 g indicating a weight loss of 15.7%. Average vanadium oxidation state determination of the 10 wt. % fatty acid mixture 6.35 mm shaped tablets showed a value of 3.98. After nitrogen purge of the tablets at 240° C., the recovered overstripped sample was found to have an average vanadium oxidation state of 3.56.

The catalyst system was then treated as follows:

About 61.9 gms of the catalyst tablets were placed into a box oven, purged with nitrogen gas and heated to approximately 220° C., and held for 40 minutes. Then a 40 liter/min 50:50 mixture of steam:nitrogen was introduced.

Next, air was incremented in two steps over ≅60 minutes to give a gas composition of 6:50:44 volume per cent oxygen:nitrogen:steam, and the temperature was raised to 260° C. after the last increment, where it was held for ≅30 minutes. Next, the temperature was raised at a controlled rate of 4° C./min to ≅425° C. and held there for ≅1 hour; then the atmosphere in the oven was changed to 50 volume percent nitrogen and 50 volume percent steam and maintained at ≅425° C. for 6 hours. The tray of catalyst structures was then allowed to cool to room temperature while the oven was purged with dry nitrogen. The properties of the thusly prepared catalysts are summarized in Table 5.

TABLE 5

| WT % PMA | TOTAL PORE VOLUME CC/GM | PORE DISTRIBUTION | | PORES >10μ | PORES >0.8μ | PV (10 – .8μ) CC/G |
|---|---|---|---|---|---|---|
| | | >10μ CC/G | >.8μ CC/G | | | |
| | 0.3579 | 0.009 | 0.039 | 2.5% | 10.9% | 0.030 |

NOTE: PERFORMANCE DATA IS AS FOLLOWS:
% BCY    BATH, T
52.2     431

As can be seen from the data, the overstripping process resulted in a VPO catalyst with high total porosity, but with an insufficient percentage of pores greater than 10 microns. The catalyst exhibited a low activity and a low maleic anhydride yield.

EXAMPLE 6

Methylcellulose Comparative Example (3434152 and 4972315)

Grey-black precursor powder as described in Example 1 (500 g) was dry blended with Dow A4M methylcellulose powder (56.2 g) having a mean particle size of 116 microns and graphite (5.6 g). The blend was composed of 10.0% methylcellulose (MC) and 1.0% graphite by weight. The powder was tableted using a Stokes 512 Rotary Tableting press to give 12.7 mm diameter slugs having a length of 6.26 mm and a slug density of about 1.32 g/cc. These slugs were granulated into less than 1 mm particulates which were then tableted to produce 6.35 mm diameter cylinders having three equidistant grooves etched in the longitudinal surface as in Example 1. About 53.6 gms of the methylcellulose-containing tablets and ≅30 grams of 15% fatty acid (FA) containing tablets of Example 1 were placed in trays with thermocouples in an oven purged with ≅15 liters per minute of nitrogen, and the oven temperature was set to 240° C. The temperature and atmosphere changes went according to Table 6A:

TABLE 6A

| TIME HOURS | OVEN SET | LITERS PER MINUTE | | | GAS COMPOSITION | | |
|---|---|---|---|---|---|---|---|
| | | N2 | AIR | STEAM | % N2 | % O2 | % STEAM |
| 0 | 240 | 16 | 0 | 0 | 100 | 0 | 0 |
| 1.4 | 240 | 15 | 0 | 20 | 43 | | 57 |
| 1.8 | 240 | 15 | 2 | 20 | 45 | 1 | 54 |
| 2.0 | 240 | 15 | 6 | 20 | 48 | 3 | 49 |
| 2.1 | 240 | 15 | 10 | 20 | 51 | 4.6 | 44.4 |
| 2.2 | 240 | 10 | 13 | 20 | 47 | 6.5 | 46.5 |
| 2.3 | 240 | 0 | 19 | 20 | 39 | 10 | 51 |
| 2.5 | 250 | 0 | 19 | 20 | 39 | 10 | 51 |
| 2.6 | 260 | 0 | 19 | 20 | 39 | 10 | 51 |
| 3.3 | 260 | 0 | 19 | 20 | 39 | 10 | 51 |
| 3.4 | 260 | 0 | 5 | 30 | 11 | 3 | 86 |
| 3.5 | 260 | 0 | 5 | 30 | 11 | 3 | 86 |

Begin Ramp of 4C/min to 425° C.

Figure 14:
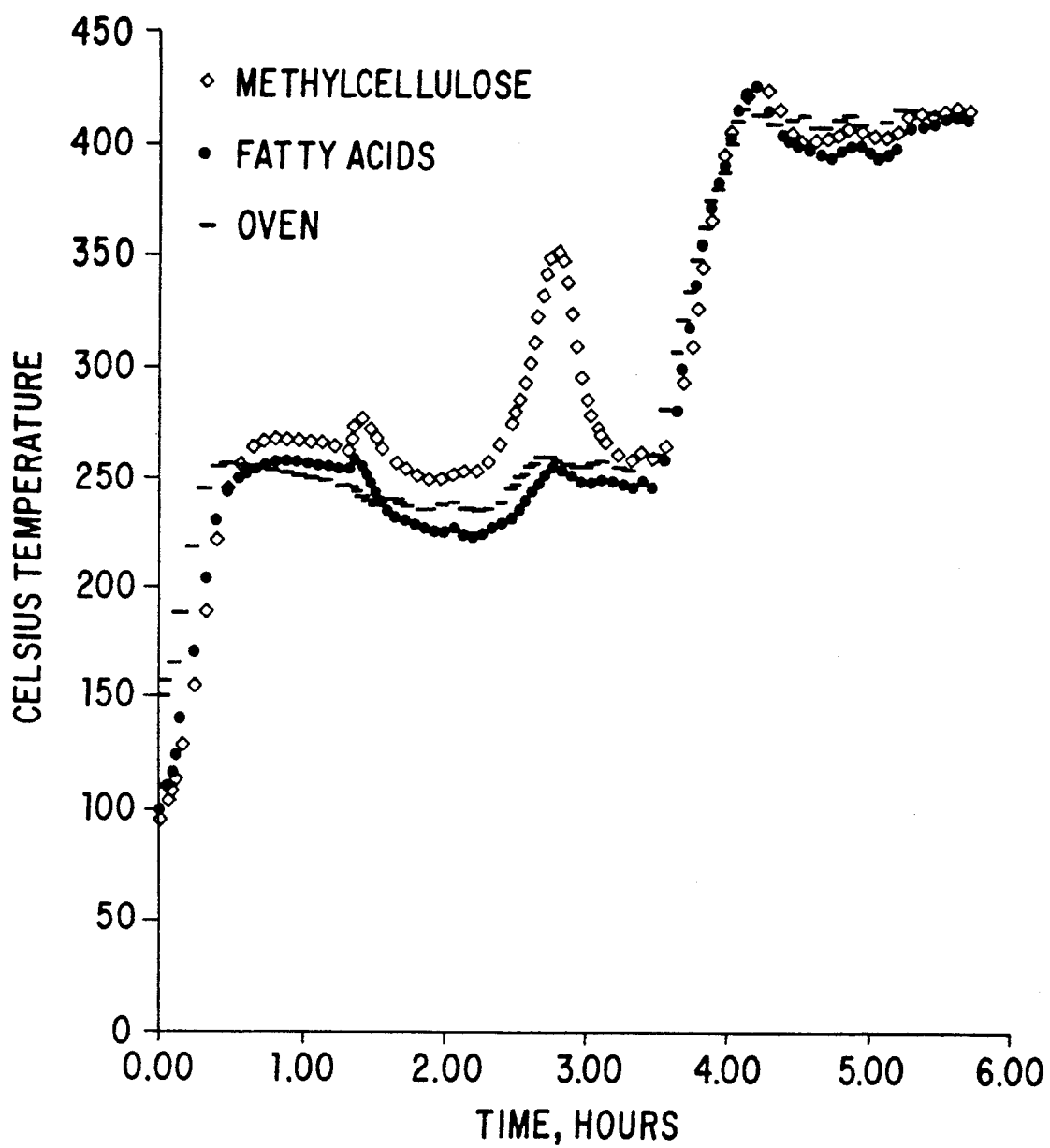
FIG. 14 contains plots of sample temperature and oven temperature vs. time for stripping fatty acid and methylcellulose pore builders, respectively, from a modified precursor composition, as described in Example 6.

The temperature recordings for the two samples and the oven are shown in FIG. 14. The amount of time the methylcellulose-containing sample exothermed above 325° C. during burn out was 13 minutes.

The tablet and pore data for the two samples are summarized in Table 6B.

TABLE 6B

| WT % PMA. | TOTAL PORE VOLUME CC/GM | PORE DISTRIBUTION >10μ CC/G | >0.8μ CC/G | PORES >10μ | PORES >0.8μ | PV(10 − .8μ) CC/G | CRUSH LBS |
|---|---|---|---|---|---|---|---|
| 10MC | 0.4955 | 0.007 | 0.076 | 1.4% | 15.3% | 0.069 | 2 |
| 15FA | 0.5315 | 0.181 | 0.210 | 34.1 | 39.5 | 0.029 | 4 |

NOTE: Performance data are as follows:
Sample  % BCY  BATH, T
MC      52.5   421° C.
FA      57.5   412° C.

As can be seen from the data, the excessive exotherm of the MC containing catalyst resulted in a poor performing, high porosity catalyst lacking both crush strength and sufficient porosity greater than 10 microns.

EXAMPLE 7

On the bottom of an ACL sublimator vessel was placed 3.03 gms of 3.97 mm trilobes containing 12% fatty acid mixture prepared according to Example 2, and a small nitrogen purge was established. The sublimator rested inside an appropriately sized heating mantle. A slush of 2-propanol and dry ice was used in the sublimator cold finger. A Type K thermocouple was placed adjacent to the bottom of the sublimator to record temperatures. After purging with nitrogen for 30 minutes, the vessel was heated to about 260° C. and maintained for 70 minutes. During this period of time, a white solid deposited on the cold finger. After cooling the vessel, 2.62 gms of tablets were recovered corresponding to a 13.5% weight loss. The white power was recovered from the cold finger surface, and its melting point was determined by DSC to be 54° C., the same as the fatty acid starting mixture (composition of a fatty acid mixture in % by weight-palmitic [50%]; stearic acid [45.5%]; myristic acid [4.55%] having a melting point of 54.5° to 55.5° C. and a boiling point of 386° C. at 760 mm mercury). The pore data in Table 7 illustrates the desired porosity has been achieved prior to thermal processing above 300° C.

TABLE 7

| WT % PMA | TOTAL PORE VOLUME CC/GM | PORE DISTRIBUTION >10μ CC/G | >.8μ CC/G | PORES <10μ | PORES >0.8μ | PV (10 − .8μ) CC/G |
|---|---|---|---|---|---|---|
| 12 | 0.2258 | 0.106 | 0.1163 | 46.9 | 51.5 | 0.0103 |

The pore builder was volatilized from catalyst substantially molecularly intact, and the desired pore features were achieved. Thus, this PMA can be recovered and recycled. The advantages of removing pore builder in an inert atmosphere at temperatures below 300° C., or optionally at reduced pressures and even lower temperatures, are (1) minimal generation of unwanted by-products that would be classified as waste, and (2) no interference with the calcination/ANST chemistry due to uncontrolled thermal excursions from combustion of the contained organic material.

EXAMPLE 8

Grey-black precursor powder was dry blended with 10.0% by weight of three fatty acid pore modification agents (PMA) having mean particle diameters from 68 to 455 microns. The powders were tableted using a Stokes 512 Rotary Tableting press to produce 12.7 mm diameter slugs having a length of 6.26 mm and a slug density around 1.32 g/cc. The slugs were granulated to less than 1 mm particulates and then tableted to give 6.35 mm diameter cylinders having three equidistant grooves etched along the longitudinal surfaces as described in Example 1. The tablets were formed with tablet densities of from 1.74 to 1.92 g/cc. A comparative sample was also prepared using 4.0% by weight graphite instead of a fatty acid mixture.

Each of the fatty acid containing tablet samples was loaded into a 16-mesh stainless steel cylinder as described in Example 5. The cylinder contained a thermowell in which a thermocouple was located. Air and nitrogen at 0.30 and 2.65 standard liters per min (SLPM), respectively, were passed through the sample while it was thermally equilibrated to about 150° C. in an upflow reactor tube. When a minimum sample bed temperature of about 125° C. was reached, steam was passed through sample bed at 2.95 SLPM. The total gas flow rate was 5.90 SLPM with a composition of 5% by volume air, 45% by volume nitrogen, and 50% by volume steam. The gas temperature was adjusted by an electronically heated beaded heater wrapped around the reactor shell. The beaded heater was connected to a programmable controller that could be operated either in a manual mode (with a shell set point temperature of 150° C.) or a programmed mode. The programmed mode was entered after thermal equilibration of the sample and cylinder. The following sequence was used for each of the fatty acid containing samples: 150° C., 1 hr. hold; 20 min. ramp to 220° C.; 220° C.; 220° C., 1 hr. hold; 15 min. ramp to 240° C., 1 hr. hold; 1. hr. ramp to 260° C., 1 hr. hold; 48 hr. ramp down to 150° C. during which time the controller was returned to the manual 150° C. set point. The sample cylinder was removed at temperatures between 150° C. and 230° C. with the steam flow shut off about 1 min. before removal. Observed weight losses for four 10.0% fatty acid containing samples ranged from 96.6 to 108.2% of the initial fatty acid weight blended into the tablets.

The fatty acid stripped samples were then subjected to activation in a box oven under a nitrogen gas purge at about 15 SLPM. Thermocouples were located within sample tablet beds in wire mesh baskets affixed to wire mesh trays. The oven was heated under the control of a programmable controller to 260° C. at 4°/min. then held at 260° for 1 hr. After a bed temperature around 150° C. was reached, steam was added to the oven at 20 SLPM. During 1 hr. hold at 260° C., air was added to the gas stream at 10 SLPM while the nitrogen purge adjusted to 10 SLPM. The gas composition was then 25% air, 25% nitrogen, and 50% steam. The temperature was then ramped to 425° C. at 4°/min. and held at 425° C. for 7 hr. After 1 hr. at 425° C., the air was turned off.

The 4% graphite sample was activated in an identical fashion to that of the fatty acid stripped samples described above.

Tableted properties of the formed and activated samples are summarized in Table 8A. Mercury intrusion porosimetry data collected on the activated samples are collected in Table 8B. Note that the samples prepared with 10% Type E fatty acid mixture and 4% graphite failed to show more than 8% of their total pore volume greater than 0.8 microns. Catalyst performance data are shown in Table 8C. Catalysts of this invention prepared from pore modification agents having mean particle diameters between 100 and 550 microns show significant improvements in both the maleic yield and bath temperature over graphite-containing catalysts.

TABLE 8A

| Catalyst No. | PMA | Side Crush, Lbs. Formed | Side Crush, Lbs. Act. | Tab Dens., g/cc Formed | Tab Dens., g/cc Act. |
|---|---|---|---|---|---|
| XX | Type E, 68μ | 15.0 | 11.0 | 1.92 | 1.56 |
| XXI | Type M, 290μ | 19.0 | 8.0 | 1.92 | 1.55 |
| XXII | Type P, 455μ | 14.0 | 8.0 | 1.89 | 1.49 |
| XXIII | Type P, 455μ | 11.0 | 6.7 | 1.74 | 1.38 |
| XXIV | None | 9.0 | 10.4 | 1.65 | 1.45 |

TABLE 8B

| Catalyst No. | PMA | Total Pore Volume, cc/g | Pore Distribution >10μ, cc/g | Pore Distribution >0.8μ, cc/g | % Pores, >10μ | % Pores 0.8μ | 0.8 – 10μ Pore Vol |
|---|---|---|---|---|---|---|---|
| XX | Type E 68μ | 0.3461 | 0.0123 | 0.0259 | 3.55 | 7.48 | 0.0136 |
| XXI | Type M 290μ | 0.3532 | 0.0559 | 0.0872 | 15.83 | 24.69 | 0.0313 |
| XXII | Type P 455μ | 0.3616 | 0.0705 | 0.0980 | 19.50 | 27.10 | 0.0275 |
| XXIII | Type P 455μ | 0.4120 | 0.0642 | 0.0941 | 15.58 | 22.84 | 0.0299 |
| XXIV | None | 0.3396 | 0.0018 | 0.0019 | 0.53 | 0.56 | 0.0001 |

TABLE 8C

| Catalyst No. | PMA | Catalyst Performance % BC Yield | Catalyst Performance Bath Temp., Deg-C. |
|---|---|---|---|
| XX | Type E, 68μ | 56.2 | 416 |
| XXI | Type M, 290μ | 57.8 | 410 |
| XXII | Type P, 455μ | 57.7 | 411 |
| XXIII | Type P, 455μ | 58.2 | 410 |
| XXIV | None | 56.2 | 420 |

We claim:

1. An activated porous phosphorus/vanadium oxide catalyst adapted for the catalytic oxidation of a hydrocarbon to produce a carboxylic acid anhydride, said catalyst comprising shaped bodies having a phosphorus/vanadium atom ratio of from about 1.05 to about 1.15, a B.E.T. surface area of at least about 20 m$^2$/g, an average vanadium oxidation state of between about 4.06 and about 4.3, a total pore volume of at least about 0.15 cc/g, a normalized apparent shaped body density of between about 1.0 and about 2.0 g/cc, and a crush strength of at least about 4 pounds, at least about 5% of the pore volume of said catalyst being constituted of pores having a diameter of at least about 0.8 microns, and at least about 4% of the pore volume being constituted of pores having a diameter of at least about 10 microns.

2. A catalyst as set forth in claim 1 wherein each of the shaped bodies comprising said catalyst has exit holes having a diameter of at least 2 microns at the external surfaces thereof, said holes being present in a density of at least about 100 surface holes per mm$^2$, said holes being in communication with the body interior.

3. A catalyst as set forth in claim 1 wherein pores having a diameter of greater than about 0.8 microns constitute at least about 8% of the total pore volume of said catalyst.

4. A catalyst as set forth in claim 3 wherein pores having a diameter of greater than about 0.8 microns constitute between about 8% and about 50% of the total pore volume of said catalyst.

5. A catalyst as set forth in claim 4 wherein pores having a diameter of greater than about 10 microns constitute between about 6% and about 40% of the total pore volume of said catalyst.

6. A process for the preparation of a phosphorus/vanadium oxide catalyst comprising the steps of:
 (a) preparing a modified catalyst precursor composition comprising a mixture of a particulate phosphorus/vanadium oxide catalyst precursor composition and a pore modification agent in proportions sufficient to provide a pore modification agent concentration of from about 4% to about 16% by weight, said pore modification agent being subject to vaporization, decomposition or oxidation at a temperature below 300° C. without leaving a substantial residue;
 (b) forming said modified catalyst precursor composition into a predetermined shape under compression, thereby producing a shaped porous catalyst precursor body comprising said catalyst precursor composition and containing said pore modification agent;
 (c) heating the catalyst precursor body from Step (b) in an atmosphere selected from the group consisting of air, steam, inert gas, and mixtures thereof to a temperature not to exceed about 300° C., thereby removing said pore modification agent from said catalyst precursor body substantially at a temperature below 300° C. to produce a catalyst precursor body having a pore volume of at least about 0.15 cc/g, at least about 5% of the pore volume of said catalyst precursor body being constituted of pores having a diameter of at least about 0.8 microns, and at least about 4% of the pore volume is constituted of pores having a diameter of at least about 10 microns;

(d) maintaining the catalyst precursor body at the temperature of Step (c) and providing an atmosphere containing molecular oxygen, steam, and optionally an inert gas, the atmosphere being represented by the formula $$(O_2)_x(H_2O)_y(IG)_z$$

wherein IG is an inert gas and x, y, and z represent mol percent of the $O_2$, $H_2O$, and IG components, respectively, in the molecular oxygen/steam-containing atmosphere, with x having a value greater than zero (0) mol %, but less than 100 mol %, y having a value greater than zero (0) mol %, but less than 100 mol %, and z having a value representing the balance of the molecular oxygen/steam-containing atmosphere;

(e) increasing the temperature at a programmed rate of from about 2° C./min to about 12° C./min to a value effective to eliminate the water of hydration from the catalyst precursor body;

(f) adjusting the temperature from Step (e) to a value greater than 350° C., but less than 550° C., and maintaining the adjusted temperature in the molecular oxygen/steam-containing atmosphere for a time effective to provide a vanadium oxidation state of from about +4.06 to about +4.3; and (g) continuing to maintain the adjusted temperature in a nonoxidizing, steam-containing atmosphere for a time effective to complete the catalyst precursor-to-active catalyst transformation to yield the active catalyst.

7. A process as set forth in claim 6 wherein said shaped porous body is heated to a temperature of between about 150° C. and about 250° C. for removal of said pore modification agent.

8. A process as set forth in claim 6 wherein said pore modification agent is removed by vaporization.

9. A process as set forth in claim 8 wherein said pore modification agent has a vapor pressure of at least about 1 mm Hg at a temperature below 300° C., and said agent is removed by passing a stripping gas over said catalyst body at a temperature at which said vapor pressure is at least about 1 mm Hg.

10. A process as set forth in claim 9 wherein the stripping gas containing at least about 5% by volume water vapor when the temperature of said catalyst body is above the temperature at which the vapor pressure of the pore modification agent is 1 mm Hg.

11. A process as set forth in claim 10 wherein the stripping gas contains between about 20% and about 80% by volume water vapor when the temperature of said catalyst body is above the temperature at which said pore modification agent has a vapor pressure of 1 mm Hg.

12. A process as set forth in claim 11 wherein the composition of said stripping gas is such that no reaction that may occur between said agent and any component of said gas generates an exotherm sufficient to heat said body to a temperature of greater than 300° C.

13. A process as set forth in claim 12 wherein essentially complete removal of said agent is provided, without reduction of vanadium in said precursor composition to an average oxidation state of less than about 3.8, by incorporating an oxidizing gas in said stripping gas.

14. A process as set forth in claim 13 wherein oxygen is incorporated in said stripping gas so that, after 90% of said pore modification agent has been removed from said body, the proportion of oxygen in said gas is sufficient to prevent reduction of the average oxidation state of vanadium in said precursor body to less than about 3.8 but not sufficient to create a flammable mixture in said stripping gas.

15. A process as set forth in claim 9 wherein said pore modification agent is removed at a temperature below the temperature at which oxygen atoms in said precursor composition are labile and subject to abstraction.

16. A process as set forth in claim 15 wherein said pore modification agent has a vapor pressure of at least about 1 mm Hg at a temperature below the temperature at which oxygen atoms in said precursor composition are labile and subject to abstraction.

17. A process as set forth in claim 9 wherein said gas is passed through a fixed bed comprised of said shaped bodies.

18. A process as set forth in claim 17 wherein said gas exiting said bed is cooled to condense said pore modification agent.

19. A process as set forth in claim 18 wherein said pore modification agent is recovered and reused in the preparation of further shaped bodies comprising said modified precursor composition.

20. A process as set forth in claim 9 wherein said pore modification agent has a melting point below the temperature to which the shaped body is heated, whereby said agent melts and flows to the surface of said body under influence of heat, and is removed from the external surface of said body as a vapor.

21. A process as set forth in claim 20 wherein said vapor is condensed and the pore modification agent thereby recovered molecularly intact.

22. A process as set forth in claim 9 wherein said pore modification agent is selected from the group consisting of fatty acids, fatty acid esters, and polynuclear organic compounds.

23. A process as set forth in claim 7 wherein said pore modification agent is removed by oxidation or decomposition at a temperature below 300° C.

24. A process as set forth in claim 23 wherein said pore modification is removed by passing a stripping gas over said catalyst bed, said stripping gas containing an oxidizing gas in a proportion sufficient to react with said agent or the decomposition products thereof but not sufficient to create a flammable mixture in said stripping gas.

25. A process as set forth in claim 24 wherein the stripping gas containing at least about 5% by volume water vapor when the temperature of said catalyst body is above the temperature at which the vapor pressure of the pore modification agent is 1 mm Hg.

26. A process as set forth in claim 6 wherein said particulate phosphorus/vanadium oxide precursor is mixed with a particulate pore modification agent, the mean particle diameter of said pore modification agent being not greater than about two orders of magnitude different from the mean particle diameter of said precursor.

27. A process as set forth in claim 26 wherein said pore agent has a mean particle diameter of between about 50 and about 2000 microns.

28. A process as set forth in claim 27 wherein said pore modification agent has a mean particle diameter of between about 100 and about 550 microns.

29. A process as set forth in claim 28 wherein said particulate phosphorus/vanadium oxide precursor has a mean particle diameter of between about 50 and about 200 microns.

30. A process as set forth in claim 7 wherein said catalyst precursor composition corresponds to the formula $$VO(M)_m HPO_4 \cdot aH_2O \cdot b(P_2/_cO) \cdot n(organics)$$

wherein M is at least one promoter element selected from the group consisting of elements from Groups IA, IB, IIA, IIB, IIIA, IIIB, IVA, IVB, VA, VB, VIA, VIB, and VIIIA of the Periodic Table of the Elements, and mixtures thereof, m is a number from zero (0) to about 0.2, a is a number of at least about 0.5, b is a number taken to provide a P/V atom ratio of from about 1.0 to about 1.3, c is a number representing the oxidation number of phosphorus and has a value of 5, and n is a number taken to represent the weight % of intercalated organics component, and said precursor is transformed into an active catalyst represented by the formula $$(VO)_2(M)_m P_2O_7 \cdot b(P_2/_cO)$$

wherein M, m, b, and c are as defined above.

31. A process as set forth in claim 30 wherein transformation of said precursor to said active catalyst is carried out after removal of said pore modification agent from said catalyst precursor body.

32. A process as set forth in claim 6 wherein said pore modification agent is removed during Step (c) of said transformation.

33. A process as set forth in claim 32 wherein oxygen in a proportion of between about 0.1 and about 1.5% by volume is included in said atmosphere during an initial heating period of between about 0.5 and about 10 hours, and thereafter the oxygen content of said atmosphere is increased to between about 2.0 and about 5% by volume.

34. A process as set forth in claim 33 wherein said atmosphere contains at least about 5% by volume water vapor when in said initial heating period the temperature of said catalyst body is above the temperature at which the vapor pressure of the pore modification agent is 1 mm Hg.

35. A process as set forth in claim 6 wherein said pore modification agent has a melting point of between about 35° and about 100° C., and a vapor pressure greater than 1 mm Hg at a temperature below 300° C.

36. A process for the preparation of an active phosphorus/vanadium oxide catalyst comprising the steps of:
(a) preparing a modified catalyst precursor composition comprising a mixture of a particulate phosphorus/vanadium oxide catalyst precursor composition and a particulate pore modification agent in proportions sufficient to provide a pore modification agent concentration of from about 4% to about 16% by weight, the mean particulate diameter of said pore modification agent being not greater than about two orders of magnitude different from the mean particle diameter of said catalyst precursor composition;
(b) forming said modified catalyst precursor composition into a predetermined shape under compression, thereby producing a shaped porous catalyst precursor body comprising said catalyst precursor composition and containing said pore modification agent;
(c) removing said pore modification agent from said catalyst precursor body substantially at a temperature below 300° C. to produce a shaped catalyst precursor body having a pore volume of at least about 0.15 cc/g; and
(d) subjecting the shaped catalyst precursor body to heat treatment under conditions and for a time effective to transform the catalyst precursor into the active catalyst.

37. A process as set forth in claim 36 wherein said pore modification agent has a mean particle diameter of between about 50 and about 2000 microns.

38. A process as set forth in claim 37 wherein said pore modification agent has a mean particle diameter of between about 100 and about 550 microns.

39. A process as set forth in claim 37 wherein said particulate phosphorus/vanadium oxide precursor has a mean particle diameter of between about 50 and about 200 microns.

40. A process as set forth in claim 37 wherein at least about 5% of the pore volume of said body is constituted of pores having a diameter of at least about 0.8 microns, and at least about 4% of the pore volume is constituted of pores having a diameter of at least about 10 microns.

* * * * *